United States Patent
Kim et al.

(10) Patent No.: US 11,642,026 B2
(45) Date of Patent: May 9, 2023

(54) HUMAN BODY SENSING DEVICE

(71) Applicant: ELECTRONICS AND TELECOMMUNICATIONS RESEARCH INSTITUTE, Daejeon (KR)

(72) Inventors: Sung Eun Kim, Daejeon (KR); Kwang Il Oh, Daejeon (KR); Tae Wook Kang, Daejeon (KR); Hyuk Kim, Daejeon (KR); Mi Jeong Park, Sejong-si (KR); Hyung-Il Park, Daejeon (KR); Kyung Jin Byun, Daejeon (KR); Jae-Jin Lee, Daejeon (KR); In Gi Lim, Daejeon (KR)

(73) Assignee: Electronics and Telecommunications Research Institute, Daejeon (KR)

(*) Notice: Subject to any disclaimer, the term of this patent is extended or adjusted under 35 U.S.C. 154(b) by 543 days.

(21) Appl. No.: 16/794,718

(22) Filed: Feb. 19, 2020

(65) Prior Publication Data
US 2020/0260957 A1    Aug. 20, 2020

(30) Foreign Application Priority Data

Feb. 20, 2019   (KR) .................. 10-2019-0020123
Jun. 28, 2019   (KR) .................. 10-2019-0078048

(51) Int. Cl.
*A61B 5/00*   (2006.01)
*G06F 3/03*   (2006.01)
(Continued)

(52) U.S. Cl.
CPC ............ *A61B 5/0028* (2013.01); *A61B 5/117* (2013.01); *A61B 5/683* (2013.01); *G06F 3/03* (2013.01);
(Continued)

(58) Field of Classification Search
CPC ............... A61B 5/683; A61B 5/6802; A61B 2560/0209; A61B 5/117; A61B 5/0028;
(Continued)

(56) References Cited

U.S. PATENT DOCUMENTS 6,771,161 B1 *   8/2004   Doi ................ H04B 13/005
                                                  340/5.1
3,054,159 A1    11/2011   Hyoung et al.
(Continued)

FOREIGN PATENT DOCUMENTS

KR       100725228 B1    6/2007
KR     1020070061251 A    6/2007
(Continued)

OTHER PUBLICATIONS

Mi-jeong Park et al. "Understanding of HBC and How to utilize Human Body Communication", source: Information and Communication Open Lecture 34 (1 (separate vol. No. 5)), May 2017, 27-34(8 pages), KICS Information & Communication Magazine—Open Lecture Series 34(1 (separate vol. No. 5)), May 2017, 27-34 (8 pages), Publisher: Korea Institute of Communication Sciences.

*Primary Examiner* — Hong Zhou
(74) *Attorney, Agent, or Firm* — Rabin & Berdo, P.C.

(57) ABSTRACT

The human body sensing device includes a contact sensing unit that includes a sensing electrode and a signal electrode, an activation module that senses a contact with a body through the sensing electrode when the sensing electrode and the signal electrode contact the body and outputs a wake-up signal in response to the sensing of the contact, and a human body communication unit that provides a ground voltage to the signal electrode and outputs a data signal to the signal electrode when the wake-up signal from the activation module is received.

16 Claims, 20 Drawing Sheets

(51) Int. Cl.
    *G06F 3/044*         (2006.01)
    *A61B 5/117*         (2016.01)

(52) U.S. Cl.
    CPC ...... *G06F 3/044* (2013.01); *A61B 2560/0209* (2013.01)

(58) Field of Classification Search
    CPC .......... G06F 3/044; G06F 3/03; G06F 1/3231; G06F 1/163; G06F 1/3234; H04B 13/005
    See application file for complete search history.

(56) References Cited

U.S. PATENT DOCUMENTS

| | | | |
|---|---|---|---|
| 10,128,670 | B2 | 11/2018 | Ban et al. |
| 2007/0140120 | A1 | 6/2007 | Song et al. |
| 2008/0218183 | A1* | 9/2008 | Sato .................... H04M 1/0202 324/686 |
| 2008/0287061 | A1 | 11/2008 | Kim et al. |
| 2009/0115737 | A1* | 5/2009 | Toyoshima ......... G06F 3/04184 345/173 |
| 2009/0305641 | A1* | 12/2009 | Kubono ............... H04B 13/005 455/67.11 |
| 2010/0136906 | A1 | 6/2010 | Hwang et al. |
| 2011/0001724 | A1* | 1/2011 | Choi ..................... G06F 3/0416 345/174 |
| 2011/0086595 | A1* | 4/2011 | Shibata ................ H04B 13/005 455/73 |
| 2011/0299512 | A1 | 12/2011 | Fukuda |
| 2012/0003929 | A1* | 1/2012 | Hyoung ................ G06F 1/3231 455/41.1 |
| 2012/0026129 | A1* | 2/2012 | Kawakami ........... H04B 13/005 345/174 |
| 2013/0057415 | A1* | 3/2013 | Kim .................... H04B 13/005 341/20 |
| 2014/0267144 | A1 | 9/2014 | Kwon et al. |
| 2016/0165450 | A1* | 6/2016 | Hunt .................... G06F 3/0416 726/19 |
| 2017/0010674 | A1 | 1/2017 | Ide |
| 2017/0207861 | A1 | 7/2017 | Hyoung |
| 2018/0032200 | A1* | 2/2018 | Hong ................... B60Q 1/1484 |
| 2018/0209183 | A1* | 7/2018 | Ham ........................ G07C 9/00 |
| 2018/0316442 | A1* | 11/2018 | Kim ....................... H04B 13/00 |
| 2020/0064906 | A1 | 2/2020 | Cha |

FOREIGN PATENT DOCUMENTS

| | | |
|---|---|---|
| KR | 20140113073 A | 9/2014 |
| KR | 20170025086 A | 3/2017 |
| KR | 20180078164 A | 7/2018 |

\* cited by examiner

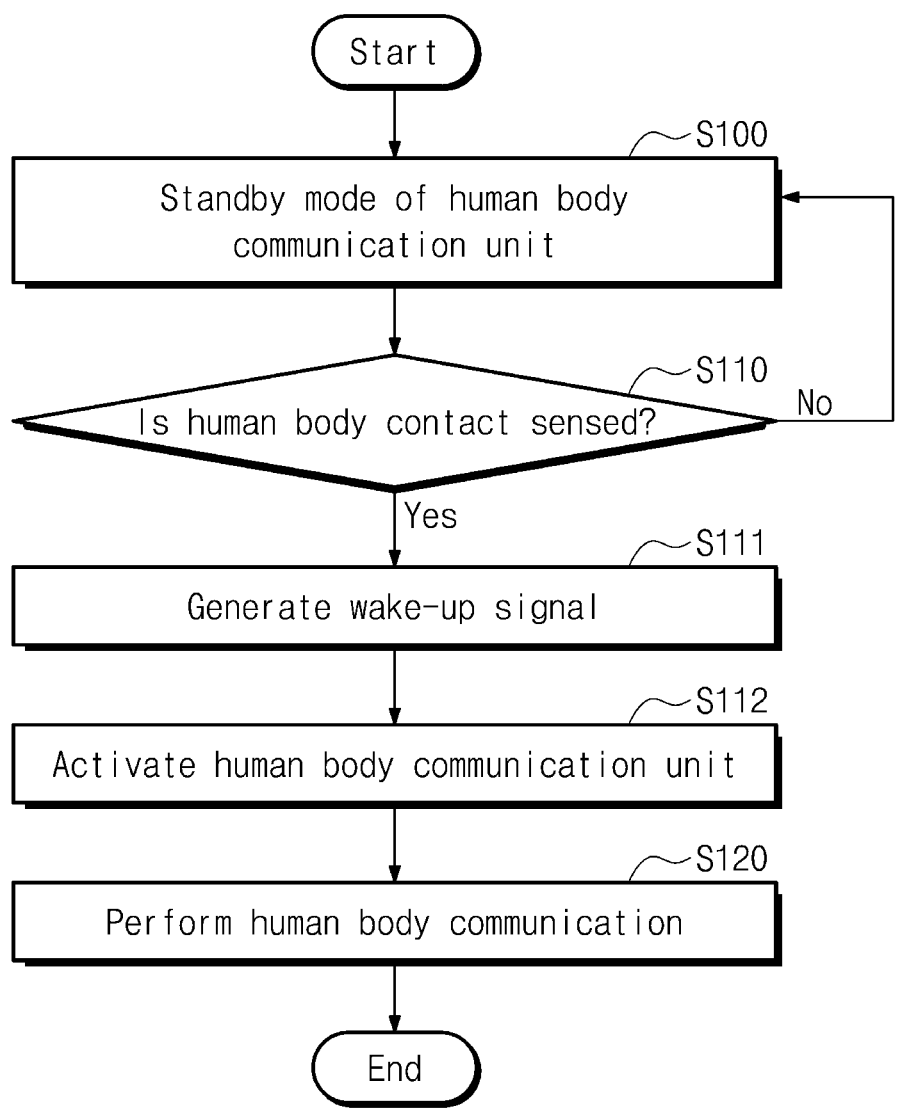

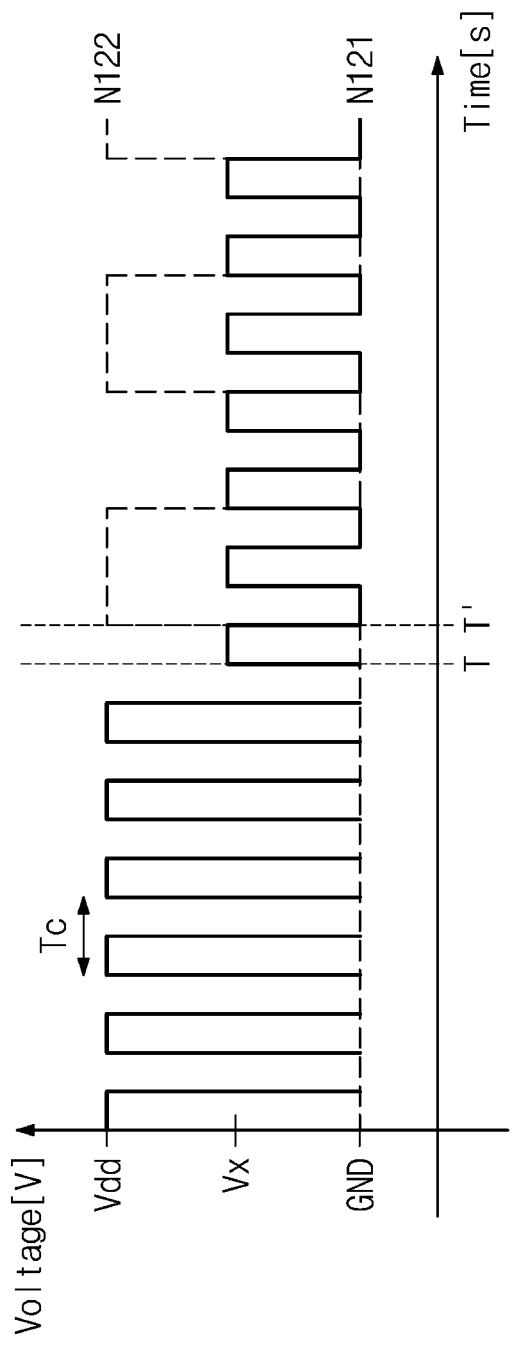

HUMAN BODY SENSING DEVICE

CROSS-REFERENCE TO RELATED APPLICATIONS

This U.S. non-provisional patent application claims priority under 35 U.S.C. § 119 of Korean Patent Application Nos. 10-2019-0020123, filed on Feb. 20, 2019, and 10-2019-0078048, filed on Jun. 28, 2019, respectively, the entire contents of which are hereby incorporated by reference.

BACKGROUND

Embodiments of the inventive concept relate to a mobile or wearable device, and more particularly, relate to a human body sensing device.

Since power supply is limited in the mobile or wearable device, there is a need to minimize power consumption. The mobile or wearable device normally operates in a standby state to minimize power consumption. When an approach of the human body is sensed, a circuit that activates the mobile or wearable device based on the sensing may be included in the mobile or wearable device.

Sensors that sense the approach of the human body are implemented in various ways. However, in this case of using a high-priced terminal such as an infrared sensor, the size of the mobile or wearable device increases, and power consumption increases. In contrast, human body sensing circuits implemented with conventional simple electronic circuits are vulnerable to external noise.

SUMMARY

The inventive concept is to solve the above technical problem, and embodiments according to the inventive concept provide a human body sensing device that may improve a reliability of a human body sensing and may reduce a manufacturing cost.

A human body sensing device according to an embodiment of the inventive concept includes a contact sensing unit that includes a sensing electrode and a signal electrode, an activation module that senses a contact with a body through the sensing electrode when the sensing electrode and the signal electrode contact the body, and outputs a wake-up signal in response to the sensing of the contact, and a human body communication unit configured to provide a ground voltage to the signal electrode and to output a data signal to the signal electrode when the wake-up signal from the activation module is received.

According to an exemplary embodiment, the activation module includes a capacitor connected to the sensing electrode and charged to a reference voltage, and a wake-up signal control module connected to the capacitor and configured to output the wake-up signal when a voltage of the capacitor is less than the reference voltage.

According to an exemplary embodiment, the human body communication unit is further configured to output an activation signal when the wake-up signal is received, wherein the wake-up signal control module includes a tri-state buffer, and wherein the tri-state buffer is configured to output the wake-up signal, and to be in a floating state when the activation signal is received.

According to an exemplary embodiment, the human body communication unit is further configured to output a clock signal, wherein the activation module includes a wake-up signal control module, and wherein the wake-up signal control module receives the clock signal, outputs the received clock signal to the sensing electrode, and outputs the wake-up signal when the clock signal output to the sensing electrode is distorted.

According to an exemplary embodiment, the wake-up signal control module switches to a floating state after the wake-up signal is output.

According to an exemplary embodiment, the human body sensing device further includes a human body matching network that receives the data signal, outputs the received data signal to the signal electrode, and performs impedance matching with the body.

According to an exemplary embodiment, the human body communication unit is further configured to operate in a first state when the wake-up signal is received and in a second state when a release of the contact with the body is sensed.

According to an exemplary embodiment, the human body sensing device further includes a ground control unit that disconnects the signal electrode from a ground point in the first state and to connect the signal electrode to the ground point in the second state.

According to an exemplary embodiment, the human body communication unit further includes a signal generator connected to a power supply voltage and a ground voltage, and wherein the signal generator is configured to output the data signal in the first state and output the ground voltage in the second state.

According to an exemplary embodiment, the human body communication unit further includes a monitor unit that monitors a voltage of the sensing electrode, and a counter unit that counts a falling edge of the voltage of the sensing electrode monitored from the monitor unit in the first state.

According to an exemplary embodiment, the human body communication unit further includes a processor that outputs information indicating that the contact with the body is maintained, when the falling edge is counted.

According to an exemplary embodiment, the processor calculates a time for which the contact is maintained, based on the information indicating that the contact is maintained and the wake-up signal.

A human body sensing device according to an embodiment of the inventive concept, includes a contact sensing unit that includes a sensing electrode and a signal electrode, a first activation module that senses a contact with a body through the sensing electrode when the sensing electrode and the signal electrode contact the body, and outputs a first wake-up signal in response to the sensing of the contact, a first motion sensing unit that senses a first motion of the body, a second activation module that outputs a second wake-up signal, based on the sensed first motion, and a human body communication unit that receives the first wake-up signal in a first state, switches to a second state based on the received first wake-up signal, receives the second wake-up signal in the second state, and outputs a data signal, and wherein the signal electrode outputs a ground voltage in the first state, and outputs the data signal to the body in the second state.

According to an exemplary embodiment, the human body sensing device further includes a second motion sensing unit that senses a second motion different from the first motion of the body, and a third activation module that outputs a third wake-up signal that is different from the first wake-up signal and the second wake-up signal to the human body communication unit, based on the sensed second motion, and wherein the data signal is output based on the first wake-up signal, the second wake-up signal, and the third wake-up signal that is output from the third activation module.

According to an exemplary embodiment, the human body communication unit outputs the data signal when both the first wake-up signal and the second wake-up signal are received.

According to an exemplary embodiment, the data signal includes a first data signal and a second data signal, and wherein the human body communication unit outputs the first data signal when the first wake-up signal is received, and outputs the second data signal when the second wake-up signal is received.

BRIEF DESCRIPTION OF THE FIGURES

The above and other objects and features of the inventive concept will become apparent by describing in detail exemplary embodiments thereof with reference to the accompanying drawings.

FIG. 3 is a flowchart describing an operation of a human body sensing device of FIG. 2.

FIGS. 6A and 6B are graphs illustrating voltages of a sensing electrode and a signal electrode of FIG. 5.

DETAILED DESCRIPTION

Embodiments of the inventive concept will be described below clearly and in detail such that those skilled in the art can easily practice the inventive concept.

In the following drawings or the detailed description, modules may be connected to others in addition to the components illustrated in drawing or described in the detailed description. The modules or components may be directly or indirectly connected. The modules or components may be communicatively connected or may be physically connected.

Components described with reference to terms such as a part or a unit, a module, a layer, etc. used in the detailed description may be implemented in the form of software, hardware, or a combination thereof. By way of example, the software may be machine code, firmware, embedded code, and application software. For example, the hardware may include electrical circuits, electronic circuits, processors, computers, integrated circuit cores, pressure sensors, inertial sensors, Micro Electro Mechanical System (MEMS), passive components, or combinations thereof.

Figure 1:
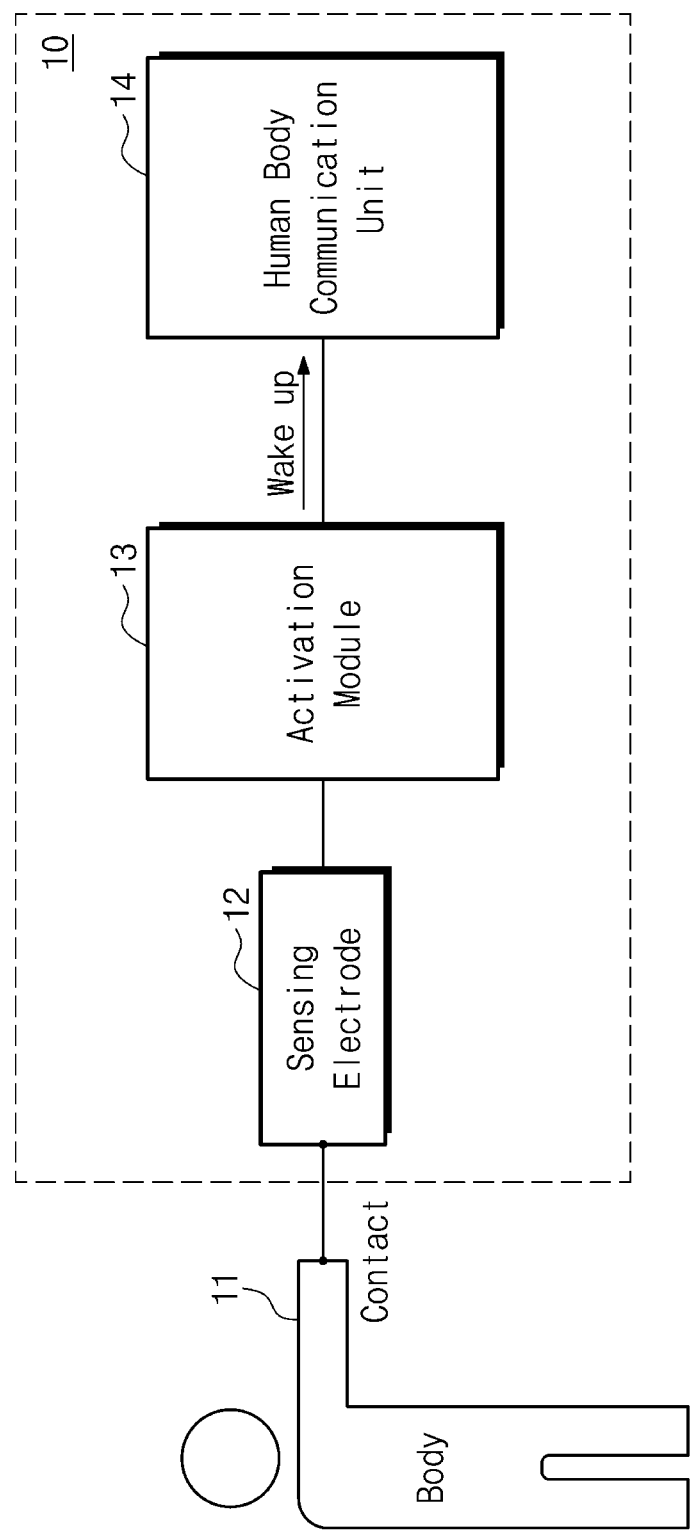
FIG. 1 is a diagram illustrating a human body sensing device.

FIG. 1 is a diagram illustrating a human body sensing device. Referring to FIG. 1, a human body sensing device 10 may include a sensing electrode 12, an activation module 13, and a human body communication unit 14. In an exemplary embodiment, the human body sensing device 10 may be a module included in a mobile device such as a smartphone, a tablet, a digital camera, etc., or may be a module included in a wearable device such as a smart watch.

The sensing electrode 12 may be in contact with a body 11. The activation module 13 may sense a contact between the sensing electrode 12 and the body 11. In response to the sensing of the contact, the activation module 13 may output a wake-up signal to the human body communication unit 14.

The human body communication unit 14 may receive the wake-up signal, and may switch a state of an operation in response to the received wake-signal. For example, the human body communication unit 14 may operate in a standby state or an active state. The standby state may be a state in which an unnecessary operation is minimized in a state in which the contact between the sensing electrode 12 and the body 11 is not sensed. The active state may be a state in which the human body communication unit 14 is activated to process data by the mobile device or the wearable device including the human body sensing device 10.

For example, when the human body sensing device 10 is not in contact with the body 11, the human body communication unit 14 may operate in the standby state. When the sensing electrode 12 is in contact with the body 11, the activation module 13 may sense the contact and may output the wake-up signal to the human body communication unit 14 in response to the sensed contact. The human body communication unit 14 may receive the wake-up signal and may switch from the standby state to the active state, based on the received wake-up signal.

As described above, the human body communication unit 14 may minimize a power consumption in the standby state when the contact with the body 11 is not sensed. Therefore, power consumption may be minimized in the mobile device or the wearable device including the human body sensing device 10.

Figure 2:
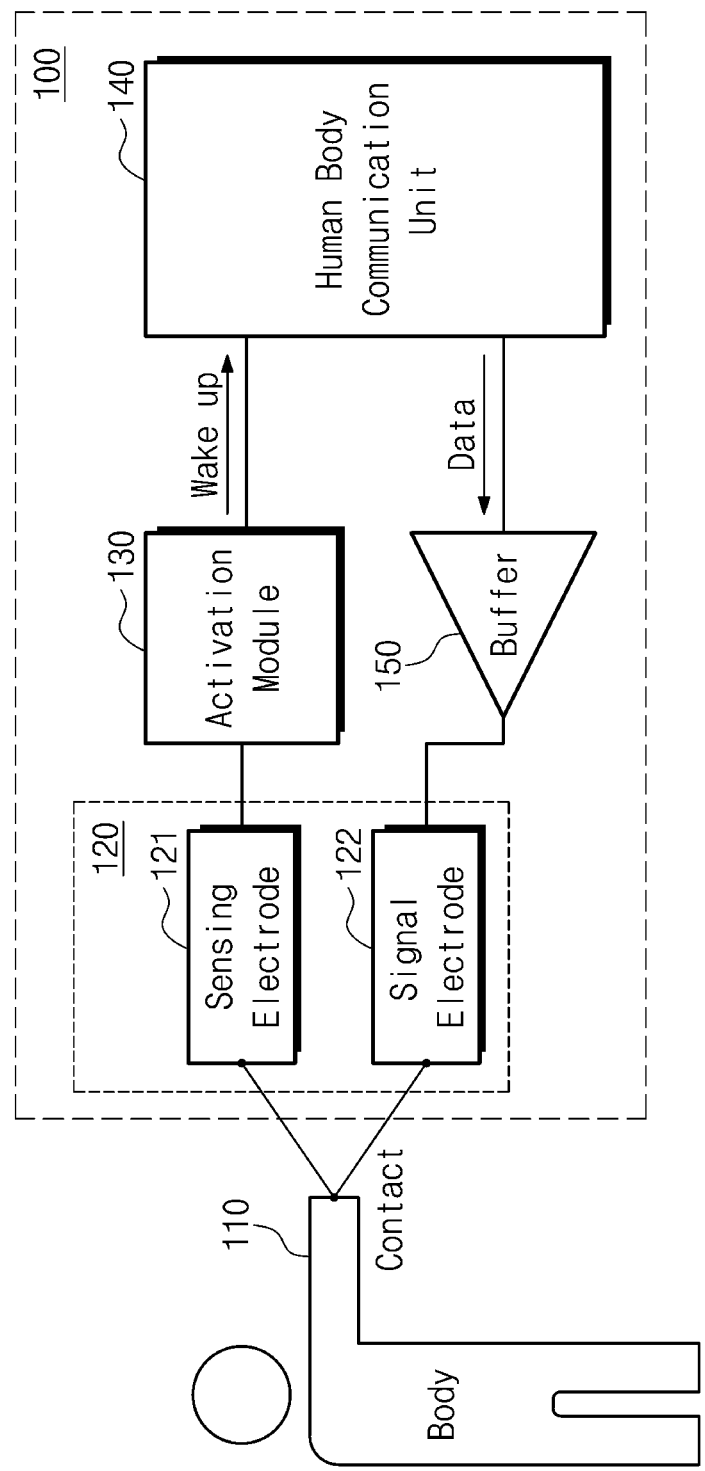
FIG. 2 is a diagram illustrating a human body sensing device according to an embodiment of the inventive concept.

FIG. 2 is a diagram illustrating a human body sensing device according to an embodiment of the inventive concept. Referring to FIG. 2, a human body sensing device 100 may include a contact sensing unit 120, an activation module 130, a human body communication unit 140, and a buffer 150.

The contact sensing unit 120 may include a sensing electrode 121 and a signal electrode 122. When the human body communication unit 140 is in the standby state, the sensing electrode 121 may sense the contact with the body 110 through the connected activation module 130. The signal electrode 122 may output a ground voltage GND. When the human body communication unit 140 is in the active state, the sensing electrode 121 may be in a floating state by an operation of the connected activation module 130. The floating state of the sensing electrode 121 may mean that the sensing electrode 121 is in a high impedance state. In this case, the signal electrode 122 may output a data signal to the body 110.

In an exemplary embodiment, the data signal may be a digital signal composed of '1' or '0'. In an exemplary embodiment, when the body 110 is in contact with the contact sensing unit 120, both the sensing electrode 121 and the signal electrode 122 may be in contact with the body 110. The sensing electrode 121 and the signal electrode 122 may be connected to each other through a human body communication channel using the body 110 as a medium.

The activation module 130 may output the wake-up signal to the human body communication unit 140 in response to the contact of the sensing electrode 121 and the body 110 when the human body communication unit 140 is in the standby state. When the human body communication unit 140 is in the active state, the activation module 130 may allow the sensing electrode 121 to be in the floating state.

In an exemplary embodiment, when the human body communication unit 140 is in the active state, the sensing electrode 121 may be in the floating state. In this case, an influence of the sensing electrode 121 on the data signal output from the signal electrode 122 may be reduced. That is, according to an exemplary embodiment of the inventive concept, a human body sensing device capable of improving a quality of the data signal may be provided.

The human body communication unit 140 may output the ground voltage GND to the buffer 150 in the standby state, and may output the data signal to the buffer 150 in the active state. The buffer 150 may be connected to a power supply voltage Vdd (refer to FIG. 7) and the ground voltage GND (refer to FIG. 7). The buffer 150 may receive the ground voltage GND or the data signal output from the human body communication unit 140. The buffer 150 may transfer the received signal to the signal electrode 122.

FIG. 3 is a flowchart describing an operation of a human body sensing device of FIG. 2. For convenience of description, an operation according to the flowchart of FIG. 3 will be described with reference to the human body sensing device 100 of FIG. 2.

Referring to FIGS. 2 and 3, in operation S100 that is performed by the human body sensing device, the contact sensing unit 120 may not be in contact with the body 110. The human body communication unit 140 may be in the standby state and may output the ground voltage GND to the signal electrode 122 through the buffer 150.

In operation S110, the activation module 130 may sense the contact between the sensing electrode 121 and the body 110. For example, when the contact with the body 110 is not sensed, the operation S100 may be repeated. In an exemplary embodiment, when the contact with the body 110 is sensed, the activation module 130 may prepare to output the wake-up signal.

In operation S111, the activation module 130 may output the wake-up signal to the human body communication unit 140. The activation module 130 may allow the sensing electrode 121 to be in the floating state.

In operation S112, the human body communication unit 140 may be activated based on the received wake-up signal. The human body communication unit 140 that is running in the standby state may switch to an active state. In this case, in contrast to the standby state, the power consumption of the human body communication unit 140 may increase, and performance functions of the human body communication unit 140 may increase.

In operation S120, the human body communication unit 140 may perform a human body communication. The human body communication unit 140 may output the data signal to the buffer 150 in the active state, the output data signal may be transferred to the body 110 through the signal electrode 122, and the human body communication may be performed based on this.

Figure 4A:
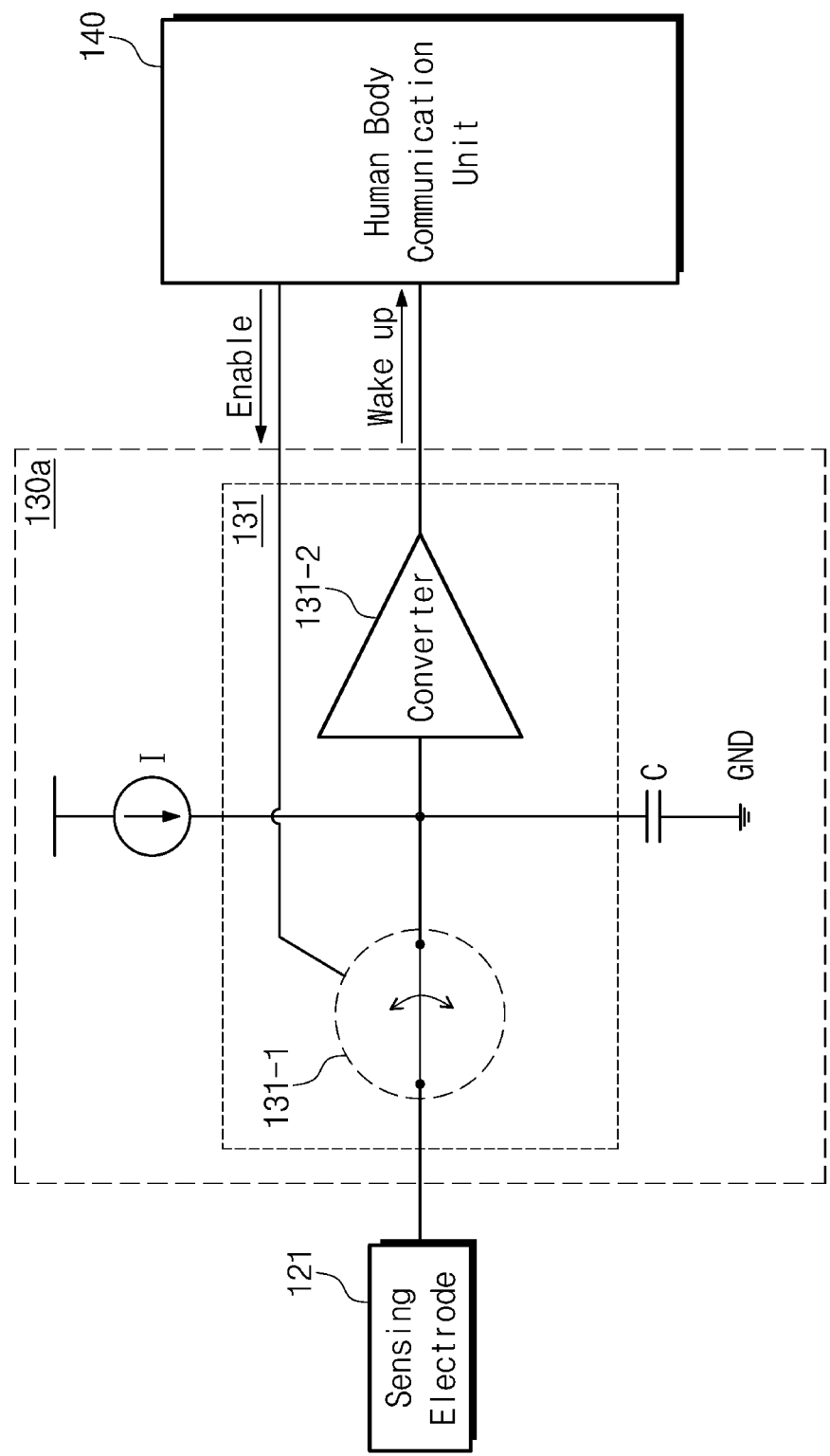
FIGS. 4A, 4B, and 4C are diagrams illustrating an operation of an activation module of FIG. 2.
Figure 4B:
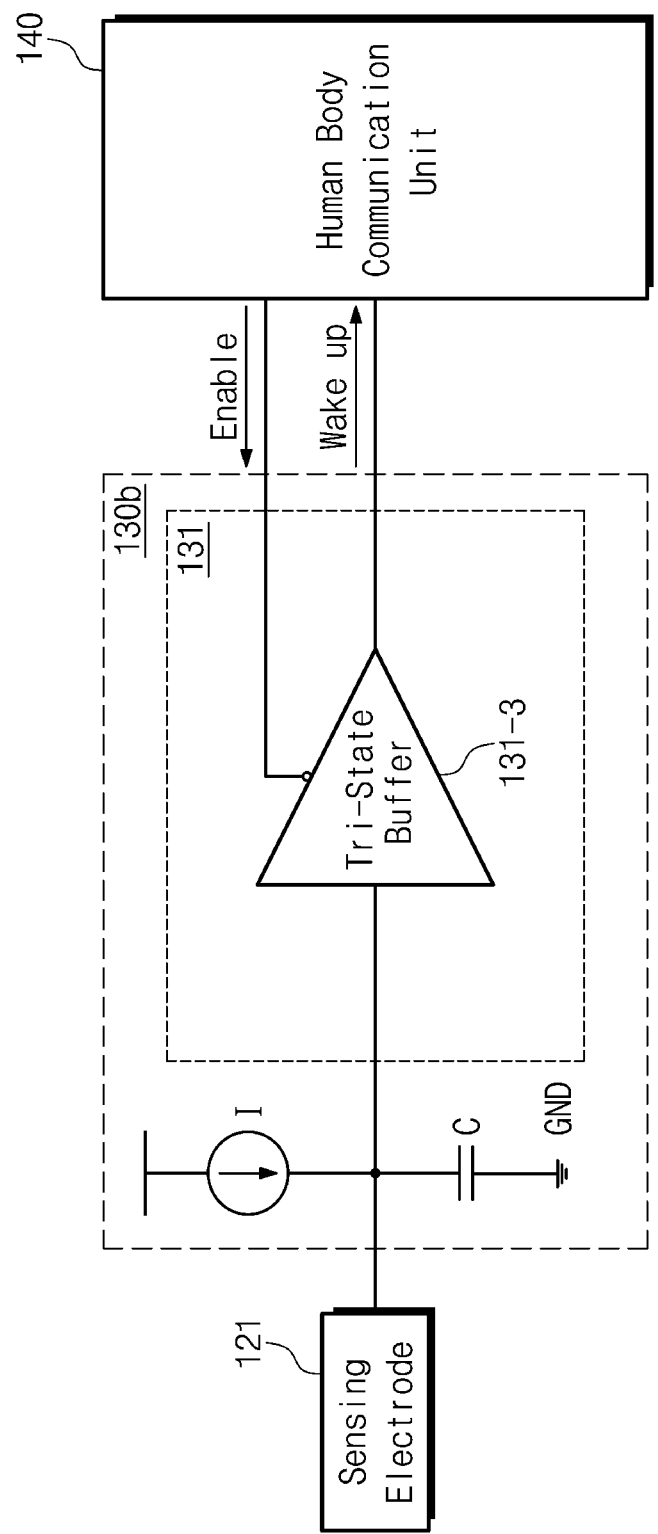
Figure 4C:
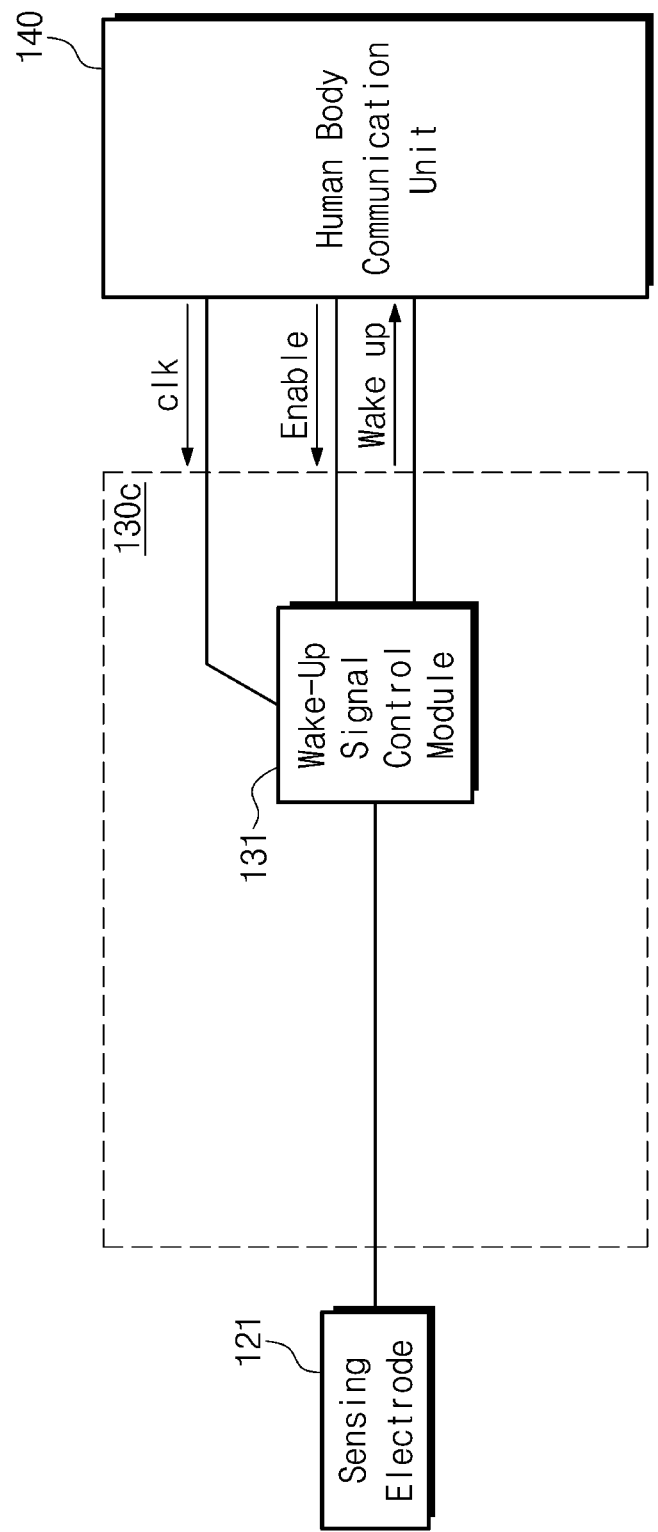

FIGS. 4A, 4B, and 4C are diagrams illustrating an operation of an activation module of FIG. 2. Referring to FIG. 4A, an activation module 130a according to an embodiment may include a current source I, a capacitor C, and a wake-up signal control module 131. The wake-up signal control module 131 may include a connection switch 131-1 and a converter 131-2. For convenience of description, the sensing electrode 121 is described above, and thus additional description will be omitted to avoid redundancy.

The current source I may be a current source for supplying a bias current to the capacitor C. The capacitor C may be connected to the sensing electrode 121, and may be a sensing capacitor that shares charge with a capacitor of the body 110 when the sensing electrode 121 contacts the body 110. The capacitor C may be charged to a reference voltage by the current source I, and may be discharged when the sensing electrode 121 contacts the body 110.

For example, the charged reference voltage in the capacitor C may be Vdd/2. When the sensing electrode 121 is in contact with the body 110, the voltage charged in the capacitor C may decrease due to the sharing charge with the capacitor of the body 110.

In an exemplary embodiment, the capacitor of the body 110 may be connected to the sensing electrode 121 and a separate electrode (e.g., the signal electrode of FIG. 2) that outputs the ground voltage GND. When the separate electrode that outputs the ground voltage GND is not connected to the capacitor of the body 110, in an environment in which a lot of noise is present in the body 110, the charge sharing between the capacitor C and the capacitor of the body 110 may be suppressed.

According to an embodiment of the inventive concept, as the sensing electrode 121 and the separate electrode that outputs the ground voltage GND are connected with the capacitor of the body 110, the capacitor of the body 110 and the capacitor C of the activation module 130a are connected in parallel to each other, thereby providing the human body sensing device that is robust to noise.

The connection switch 131-1 may be a switch connected between the sensing electrode 121 and the converter 131-2. The connection switch 131-1 may be controlled by the human body communication unit 140. For example, before the body 110 contacts the sensing electrode 121, the connection switch 131-1 may connect the sensing electrode 121 to the converter 131-2. When an enable signal is received from the human body communication unit 140, the connection switch 131-1 may disconnect the sensing electrode 121 from converter 131-2. In this case, the sensing electrode 121 may be in the floating state.

When the human body communication unit 140 is in an active state, the data signal output from the separate electrode (e.g., the signal electrode of FIG. 2) may be transferred to the sensing electrode 121 through the human body communication channel. When the sensing electrode 121 is not in a floating state, the data signal may be distorted by the capacitor C or the current source I that is connected to the sensing electrode 121. Alternatively, as the leakage current is generated through the sensing electrode 121, the data signal may be deformed.

According to an embodiment of the inventive concept, when the human body communication unit 140 is in the active state, the human body sensing device in which the distortion or deformation of the data signal is decreased by the sensing electrode 121 being in the floating state may be provided.

The converter 131-2 may be connected to the capacitor C and the human body communication unit 140 through the connection switch 131-1. The converter 131-2 may sense a decrease in the reference voltage charged in the capacitor C. The converter 131-2 may output the wake-up signal to the human body communication unit 140 in response to sensing the decrease in the reference voltage.

For example, the converter 131-2 may receive an analog signal that indicates a voltage variation in which the voltage charged in the capacitor C is less than Vdd/2. The converter 131-2 may output the wake-up signal to the human body communication unit 140 in response to the received analog signal. The wake-up signal may be a digital signal. That is, the converter 131-2 may be an analog-to-digital converter (ADC) that operates based on a decrease in a voltage of the capacitor C.

The human body communication unit 140 may be connected to the converter 131-2. The human body communication unit 140 may control the connection switch 131-1. For example, the human body communication unit 140 operating in the standby state may receive the wake-up signal from the converter 131-2. The human body communication unit 140 may switch to the active state in response to the received wake-up signal. The human body communication unit 140 that switches into the active state may output the enable signal to the connection switch 131-1. The sensing electrode 121 may be in a floating state by the connection switch 131-1 receiving the enable signal.

As described above, according to an embodiment of the inventive concept, the activation module 130a that senses the contact with the body 110, based on the voltage variation of the capacitor C charged to the reference voltage may be provided. Further, according to an embodiment of the inventive concept, when the human body communication unit 140 is in the active state, as the sensing electrode 121 and the converter 131-2 are disconnected by using the connection switch 131-1, the sensing electrode 121 may be in the floating state.

Referring to FIG. 4B, an activation module 130b according to an embodiment may include the current source I, the capacitor C, and the weak-up signal control module 131. The weak-up signal control module 131 may include a tri-state buffer 131-3. For convenience of description, the sensing electrode 121, the current source I, the capacitor C, and the human body communication unit 140 are described above, and thus additional description will be omitted to avoid redundancy.

The tri-state buffer 131-3 may be a tri-state buffer that has state of one of '1', '0', and floating. When the tri-state buffer 131-3 is in the floating state, the activation module 130b may allow the sensing electrode 121 to be in the floating state.

The tri-state buffer 131-3 may be connected to the sensing electrode 121, the capacitor C, and the human body communication unit 140. The tri-state buffer 131-3 may sense that the sensing electrode 121 contacts the body, and may output the wake-up signal to the human body communication unit 140. The tri-state buffer 131-3 may receive the enable signal from the human body communication unit 140 and may switch to the floating state.

For example, the tri-state buffer 131-3 may output the wake-up signal to the human body communication unit 140 when the voltage of the capacitor C is less than Vdd/2. The tri-state buffer 131-3 may receive the enable signal from the human body communication unit 140 in the active state. The tri-state buffer 131-3 may be in the floating state when an input terminal and an output terminal are disconnected by an inverted version of the enable signal.

As described above, according to an embodiment of the inventive concept, when the human body communication unit 140 is in the active state, the tri-state buffer 131-3 may receive the enable signal and may turn into the floating state. In this case, the sensing electrode 121 may be in the floating state.

Referring to FIG. 4C, an activation module 130c according to the embodiment may include the weak-up signal control module 131. The weak-up signal control module 131 may be connected to the sensing electrode 121 and the human body communication unit 140. The weak-up signal control module 131 may receive a clock signal clk and the enable signal. The weak-up signal control module 131 may output the weak-up signal.

According to an embodiment of the inventive concept, the wake-up signal control module 131 may sense the contact between the sensing electrode 121 and the body 110, based on the voltage variation of the sensing electrode 121. In more detail, the wake-up signal control module 131 may output the clock signal clk received from the human body communication unit 140 to the sensing electrode 121 before the sensing electrode 121 contacts the body 110. The wake-up signal control module 131 may sense that the clock signal clk is distorted when the sensing electrode 121 contacts the body 110. The wake-up signal control module 131 may output the wake-up signal to the human body communication unit 140 in response to sensing the distortion of the clock signal clk.

The wake-up signal control module 131 may switch to the floating state after the wake-up signal is output. When the wake-up signal control module 131 is in the floating state, the activation module 130c may allow the sensing electrode 121 to be in the floating state.

As described above, according to an embodiment of the inventive concept, the activation module 130c that senses the contact between the sensing electrode 121 and the body 110 based on whether the clock clk signal output to the sensing electrode 121 is distorted, may be provided.

Figure 5:
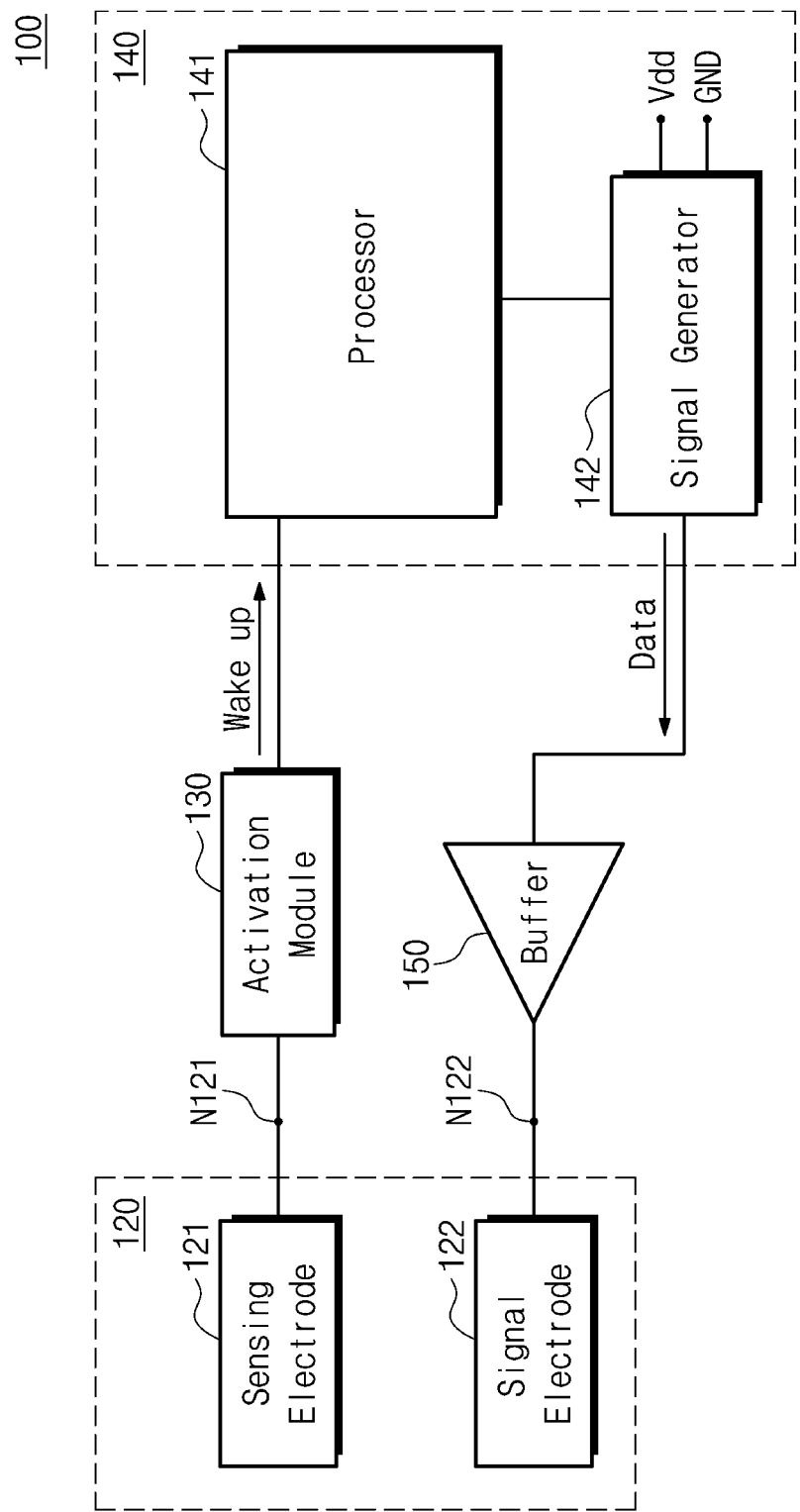
FIG. 5 is a block diagram illustrating an operation of a human body sensing device of FIG. 2.

FIG. 5 is a block diagram illustrating an operation of a human body sensing device of FIG. 2. Referring to FIG. 5, the human body sensing device 100 may include the contact sensing unit 120, the activation module 130, the human body communication unit 140, and the buffer 150. In this case, the human body communication unit 140 may include a processor 141 and a signal generator 142. For convenience of description, the contact sensing unit 120, the activation module 130, and the buffer 150 are described above, and thus additional description will be omitted to avoid redundancy.

The processor 141 may receive the wake-up signal from the activation module 130 and may control the signal generator 142, based on the received wake-up signal.

The signal generator 142 may be connected to the power supply voltage Vdd and the ground voltage GND. For example, when the human body communication unit 140 is in the standby state, the signal generator 142 may output the ground voltage GND to the buffer 150 under control of the processor 141. When the human body communication unit 140 is in the active state, the signal generator 142 may output the data signal to the buffer 150 under control of the processor 141.

The data signal output from the signal generator 142 may be the digital signal composed of '0' or '1'. In this case, the ground voltage GND may correspond to '0' and the power supply voltage Vdd may correspond to '1'. The data signal output from the signal generator 142 may be transferred to the signal electrode 122 through the buffer 150.

A sensing electrode node N121 may be a node having the same voltage as the sensing electrode 121. A signal electrode node N122 may be a node having the same voltage as the signal electrode 122. A voltage of the sensing electrode node N121 may be changed when the sensing electrode 121 contacts the body 110. The signal electrode node N122 may have the ground voltage GND when the human body communication unit 140 is in the standby state. The signal electrode node N122 may have a voltage corresponding to the data signal when the human body communication unit 140 is in the active state.

Figure 6A:
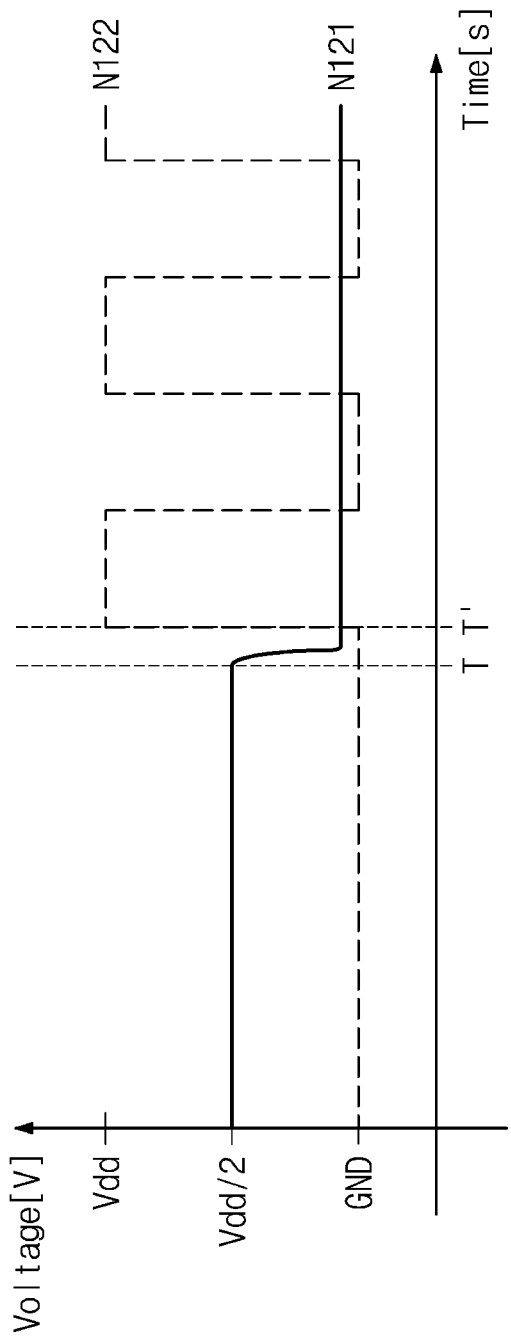

FIGS. 6A and 6B are graphs illustrating voltages of a sensing electrode and a signal electrode of FIG. 5. In FIG. 6A, voltages of the sensing electrode and the signal electrode are illustrated for an embodiment of sensing a contact with the body, based on a capacitor charged to a reference voltage.

Referring to FIGS. 5 and 6A, the contact sensing unit 120 and the body 110 may contact each other at a contact time T. Before the contact time T, the human body communication unit 140 may be in the standby state. In an interval between the contact time T and an active time T', the human body communication unit 140 may be in a state of switching from the standby state to the active state. After the active time T', the human body communication unit 140 may be in the active state.

Before the contact time T, the capacitor C of the activation module 130 may be supplied with charges, and may have the reference voltage (e.g., Vdd/2) in the standby state. In this case, the sensing electrode node N121 may have the same voltage (e.g., Vdd/2) as the voltage of the capacitor C of the activation module 130, the signal electrode node N122 may have the ground voltage GND.

In the interval between the contact time T and the active time T', the voltage of the sensing electrode node N121 may be decreased, and the activation module 130 may output the wake-up signal. For example, when the contact sensing unit 120 is in contact with the body 110 at the contact time T, the voltage of the capacitor C of the activation module 130 may be decreased through the sharing charge with the capacitor of the body 110. As a result, the voltage of the sensing electrode node N121 may be decreased.

While the body 110 is in contact with the contact sensing unit 120, as the signal electrode 122 outputs the ground voltage GND, the charge in the capacitor C of the activation module 130 may be reliably removed. As described above, the human body sensing device 100 may have characteristics that are robust to external noise.

When the separate electrode such as the signal electrode 122, and the sensing electrode 121 does not contact the body 110, or when the signal electrode node N122 does not have a voltage (e.g., GND) sufficiently less than the reference voltage (e.g., Vdd/2), even when the sensing electrode 121 contacts the body 110, the voltage of the sensing electrode node N121 may not be sufficiently reduced.

After the active time T', the signal generator 142 may output the data signal to the buffer 150. Since the signal electrode node N122 outputs the data signal received through the buffer 150, the signal electrode node N122 may output the power supply voltage Vdd or the ground voltage GND.

For simplicity of illustration, after the active time T', the voltage variation of the sensing electrode node N121 due to the voltage variation of the signal electrode node N122 is omitted in FIG. 6A. As described above, FIG. 6A is a graph illustrating the voltage of the sensing electrode node N121 and the voltage of the signal electrode node N122 to explain a contact sensing operation. After the contact, the voltage of the sensing electrode node N121 and the voltage of the signal electrode node N122 will be described later with reference to FIG. 8.

In FIG. 6B, the voltages of the sensing electrode and the signal electrode are illustrated for an embodiment of sensing the contact with the body based on the distortion of the clock signal clk. An operation of the human body sensing device according to an embodiment of the inventive concept will be described with reference to FIGS. 5 and 6B for convenience of description. Although not illustrated in FIG. 5, the processor 141 may output the clock signal clk having a uniform period Tc to the sensing electrode node N121. The contact time T may be a time during which the contact sensing unit 120 is in contact with the body. The active time T' may be a time at which the human body communication unit 140 switches from the standby state to the active state.

Before the contact time T, the sensing electrode node N121 may have a voltage (e.g., Vdd or GND) corresponding to the clock signal clk having a uniform period Tc. The signal electrode node N122 may have the ground voltage GND.

In the interval between the contact time T and the active time T', the sensing electrode node N121 may have a voltage corresponding to the distorted clock signal clk. For example, the voltage corresponding to state '1' may be attenuated from the power supply voltage Vdd to a distortion voltage Vx. In this case, the activation module 130 may sense the distortion of the clock signal clk. The activation module 130 may output the wake-up signal to the processor 141, based on the sensed result.

After the active time T', the sensing electrode node N121 may have a voltage corresponding to the distorted clock signal clk (e.g., Vx or GND) until the contact of the contact sensing unit 120 and the body is released. As the data signal received through the buffer 150 is output from the signal electrode node N122, the signal electrode node N122 may have the power supply voltage Vdd or the ground voltage GND.

While the contact between the contact sensing unit 120 and the body is maintained, because the sensing electrode 121 and the signal electrode 122 are connected with each other through the human body communication channel, the voltage variation of the signal electrode node N122 may affect the voltage of the sensing electrode node N121. For the simplicity of illustration, how the voltage of the sensing electrode node N121 varies depending on the voltage variation of the signal electrode node N122 is omitted in FIG. 6B. In addition, in FIG. 6B, after the active time T', voltage variations of the sensing electrode node N121 and the signal electrode node N122 according to release of the contact between the contact sensing unit 120 and the body are omitted.

Figure 7:
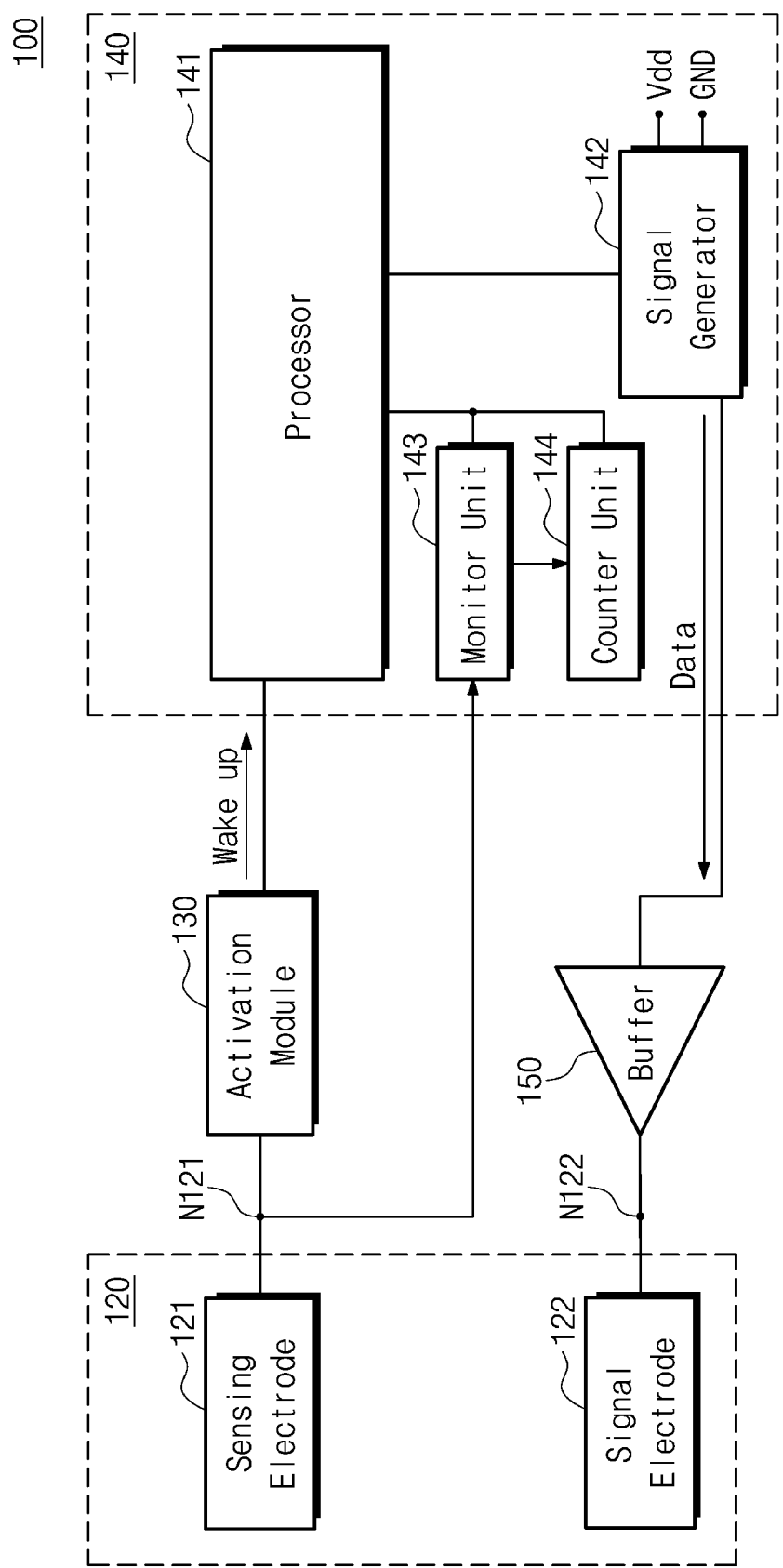
FIG. 7 is a block diagram illustrating an operation in which a human body sensing device of FIG. 2 calculates a contact time.

FIG. 7 is a block diagram illustrating an operation in which a human body sensing device of FIG. 2 calculates a contact time. Referring to FIG. 7, the human body communication unit 140 may include the processor 141, the signal generator 142, a monitor unit 143, and a counter unit 144.

For convenience of description, the contact sensing unit 120, the activation module 130, and the buffer 150 are described above, and thus additional description will be omitted to avoid redundancy.

The processor 141 may control the signal generator 142, the monitor unit 143, and the counter unit 144. The signal generator 142 may output the data signal that is periodically triggered from the power supply voltage Vdd to the ground voltage GND. Based on the data signal, it may be determined whether the contact with the body is maintained. In addition, a time when the contact with the body is maintained may be calculated based on the data signal and the wake-up signal that is output by the activation module 130.

In an exemplary embodiment, the processor 141 receiving the wake-up signal may control the signal generator 142 to output the data signal every 10 seconds. In an exemplary embodiment, when the contact is maintained for 1 hour or more, the processor 141 may control the signal generator 142 to output the data signal every 10 minutes.

The monitor unit 143 may monitor the voltage of the sensing electrode node N121. The counter unit 144 may identify whether the contact between the human body sensing device 100 and the body is maintained based on the voltage of the sensing electrode node N121 monitored by the monitor unit 143. In addition, the counter unit 144 may calculate the contact time between the human body sensing device 100 and the body in conjunction with the processor 141.

Figure 8:
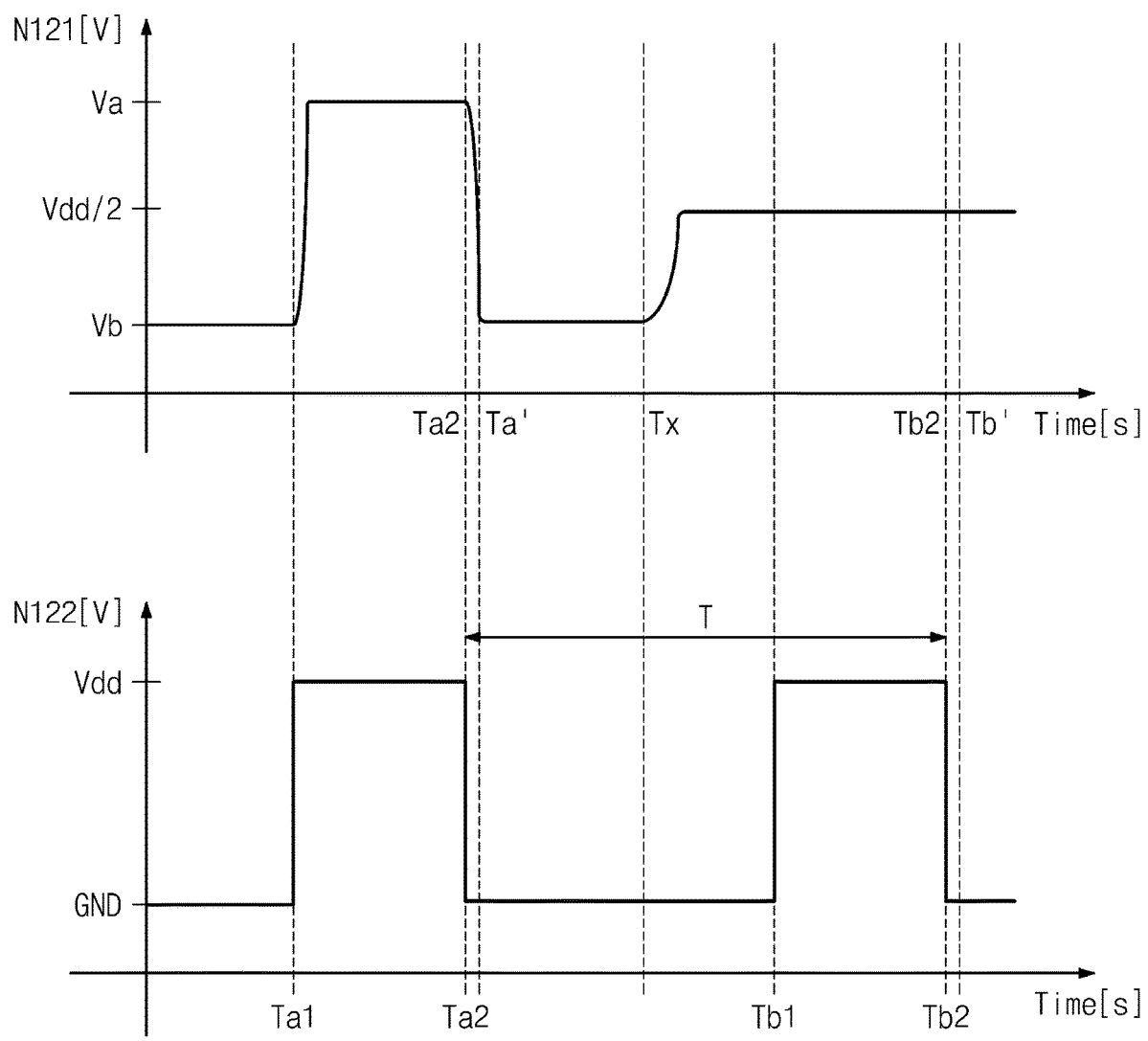
FIG. 8 illustrates graphs of a voltage of a signal electrode and a voltage of a sensing electrode of FIG. 7.

FIG. 8 illustrates graphs of a voltage of a signal electrode and a voltage of a sensing electrode of FIG. 7. For convenience of description, the graph of FIG. 8 will be described with reference to the human body sensing device 100 of FIG. 7. For convenience of description, with regard to the components described above, additional description will be omitted to avoid redundancy.

Referring to FIGS. 7 and 8, the voltage of the signal electrode node N122 may be periodically triggered from the power supply voltage Vdd to the ground voltage GND. For example, the voltage of the signal electrode node N122 may rise at a first rising time Ta1 and may fall at a first falling time Ta2. Under control of the processor 141, a period T during which the voltage of the signal electrode node N122 rises and falls repeatedly may be faster or slower.

The voltage of the sensing electrode node N121 may vary depending on the voltage variation of the signal electrode node N122. For example, when the voltage of the signal electrode node N122 increases at the first rising time Ta1, the voltage of the sensing electrode node N121 connected through the body with the signal electrode node N122 may increase. When the voltage of the signal electrode node N122 falls at the first falling time Ta2, the voltage of the sensing electrode node N121 may decrease.

In an exemplary embodiment, while the contact between the contact sensing unit 120 and the body is maintained, when the data signal is output from the signal electrode 122, a falling edge may occur at the sensing electrode node N121.

In detail, the voltage of the sensing electrode node N121 may be a first voltage Va at the first falling time Ta2. The voltage of the sensing electrode node N121 may be a second voltage Vb at the first observation time Ta'. In this case, the monitor unit 143 may monitor the falling edge at which the voltage of the sensing electrode node N121 is lowered from the first voltage Va to the second voltage Vb.

The counter unit 144 may count the falling edge monitored by the monitor unit 143. Based on a count result, the counter 144 may identify that the contact with the body is maintained, and may calculate the body contact time in conjunction with the processor 141.

In an exemplary embodiment, after the contact between the contact sensing unit 120 and the body is released, when the data signal is output from the signal electrode 122, the falling edge may not occur at the sensing electrode node N121.

In more detail, the contact between the contact sensing unit 120 and the body may be released at a contact end time Tx. After the contact is released, the sensing electrode node N121 may have the reference voltage Vdd/2 while the charge is charged in the capacitor C of the activation module 130. Thereafter, even when the voltage of the signal electrode node N122 decreases at the second falling time Tb2, since the sensing electrode 121 and the signal electrode 122 are not connected through the body, the falling edge at which the voltage of the sensing electrode node N121 decreases may not occur at the second observation time Tb'.

In this case, the monitor unit 143 may detect an occurrence of the falling edge. The counter unit 144 may transfer information that indicates that the contact with the human body is released, to the processor 141, based on the detected result. The processor 141 may receive the information that indicates that the contact with the body is released, and may calculate a time for which the contact is maintained, based on the information about the released contact and information on the previously received wake-up signal.

Figure 9:
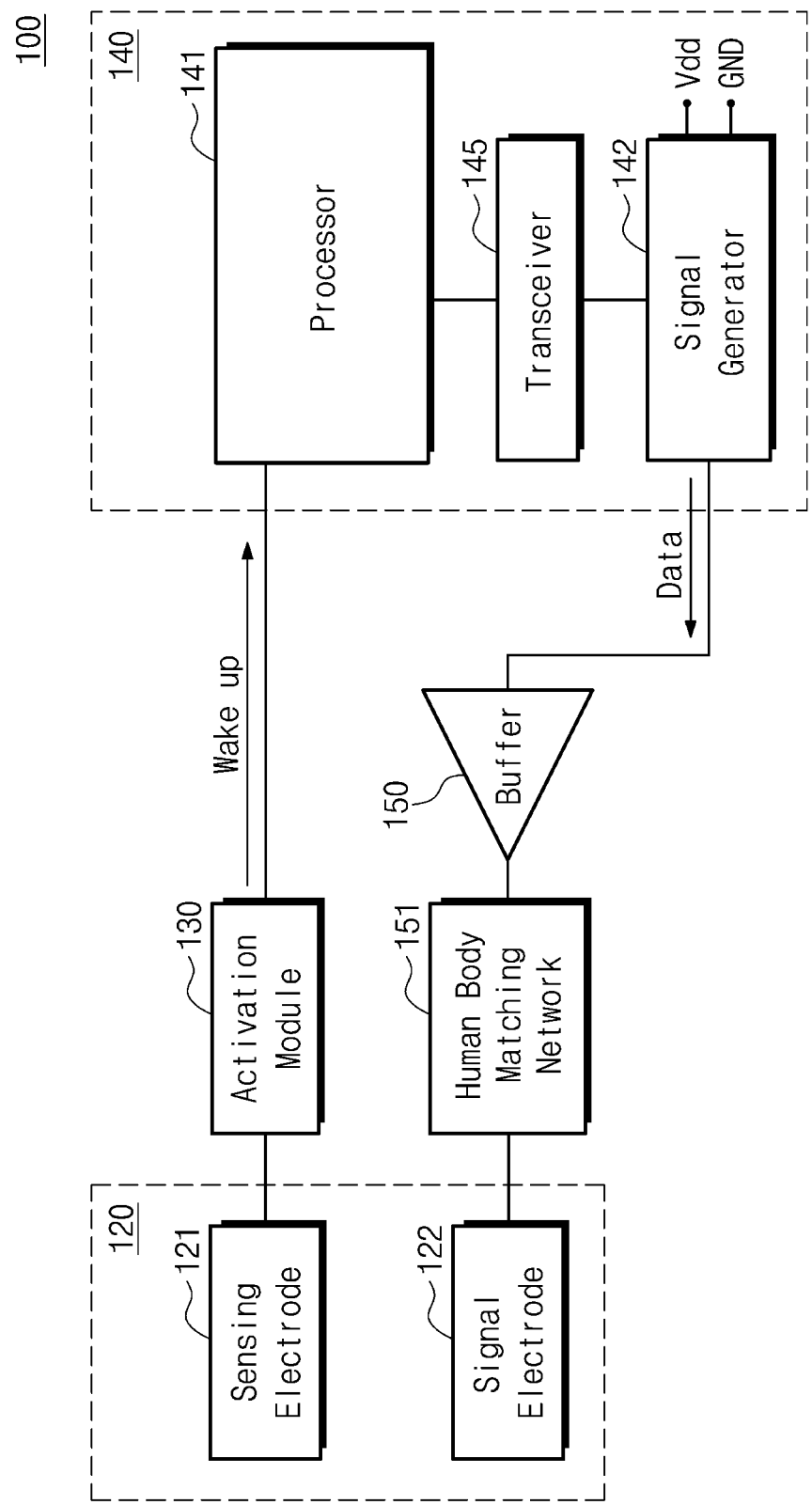
FIG. 9 is a block diagram illustrating a human body communication operation performed by a human body sensing device of FIG. 2.

FIG. 9 is a block diagram illustrating a human body communication operation performed by a human body sensing device of FIG. 2. Referring to FIG. 9, the human body communication unit 140 may include the processor 141, the signal generator 142, and a transceiver 145. The human body sensing device 100 may include a human body matching network 151 between the signal electrode 122 and the buffer 150. For convenience of description, with regard to the components described above, additional description will be omitted to avoid redundancy.

The transceiver 145 may transmit/receive a signal for human body communication. The signal generator 142 that is controlled by the transceiver 145 may output the data signal. The data signal output from the signal generator 142 may be a signal for the human body communication.

The human body matching network 151 may be connected to the signal electrode 122 and may be a network for impedance matching. In more detail, the human body matching network 151 may reduce signal reflection when the data signal output from the signal electrode 122 is transferred to the body, and may decrease the power consumption unrelated to the human body communication.

The signal electrode 122 may be utilized as a transmitting/receiving electrode in the human body communication. More specifically, the data signal that the human body communication unit 140 outputs in the active state may be a transmitting/receiving signal in the human body communication. For example, when the contact with the body is not sensed in the activation module 130, the signal electrode 122 may output the ground voltage GND. In an exemplary embodiment, when the contact with the body is detected by the activation module 130, the signal electrode 122 may output the data signal including a transmitting/receiving signal for the human body communication to the body.

Figure 10:
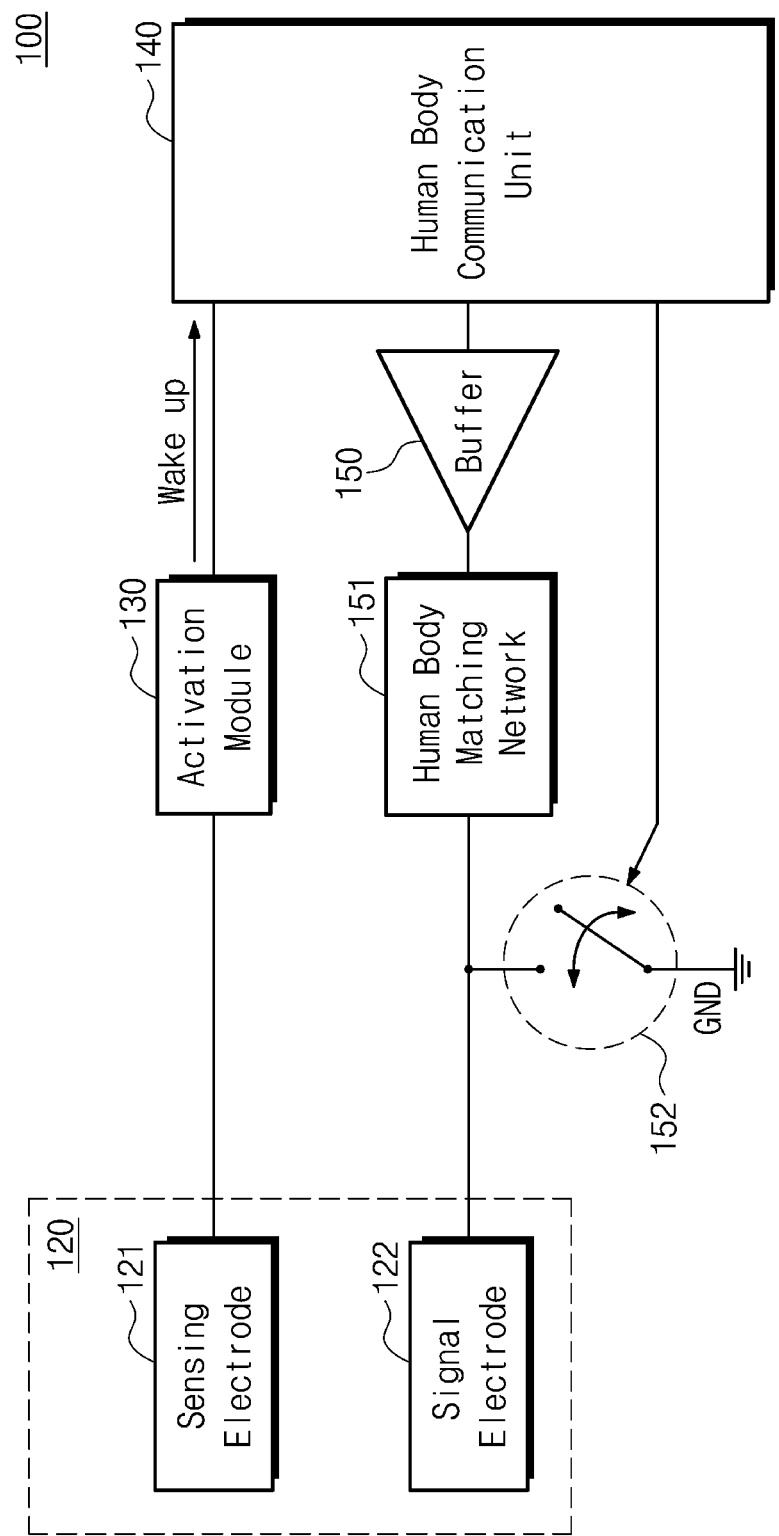
FIG. 10 is a block diagram illustrating an operation of a human body sensing device of FIG. 9.

FIG. 10 is a block diagram illustrating an operation of a human body sensing device of FIG. 9. Referring to FIG. 10, the human body sensing device 100 may include a ground controller 152 that is connected between the signal electrode 122 and the human body matching network 151. Like the human body sensing device 100 of FIG. 9, the human body sensing device 100 may output the ground voltage GND through the signal electrode 122 when the human body communication unit 140 is in the standby state.

A method in which the signal electrode 122 outputs the ground voltage GND when the human body communication unit 140 is in the standby state may include a method in which the signal generator 142 of the human body communication unit 140 outputs the ground voltage GND, like the human body sensing device 100 of FIG. 9, or a method in which the human body communication unit 140 controls the separate ground controller 152, like the human body sensing device 100 of FIG. 10.

The ground controller 152 may connect the signal electrode 122 and the ground voltage GND when the human body communication unit 140 is in the standby state, and may disconnect signal electrode 122 from the ground voltage GND when the human body communication unit 140 is in the active state. For example, the ground controller 152 may be controlled by the human body communication unit 140, and may include a ground voltage (GND) terminal and a switch. Although not illustrated in FIG. 10, in an exemplary embodiment, the ground controller 152 may be connected between the human body matching network 151 and the buffer 150 or may be connected between the buffer 150 and the human body communication unit 140.

As described above, in the case where the ground controller 152 is used separately, even when the signal generator 122 of the human body communication unit 140 does not directly output the ground voltage (GND), when the human body communication unit 140 is in a standby state, the signal electrode 122 may output the ground voltage GND. Accordingly, as in the human body sensing device 100 of FIG. 9, the human body sensing device 100 of FIG. 10 may have characteristics that are robust to external noise.

Figure 11:
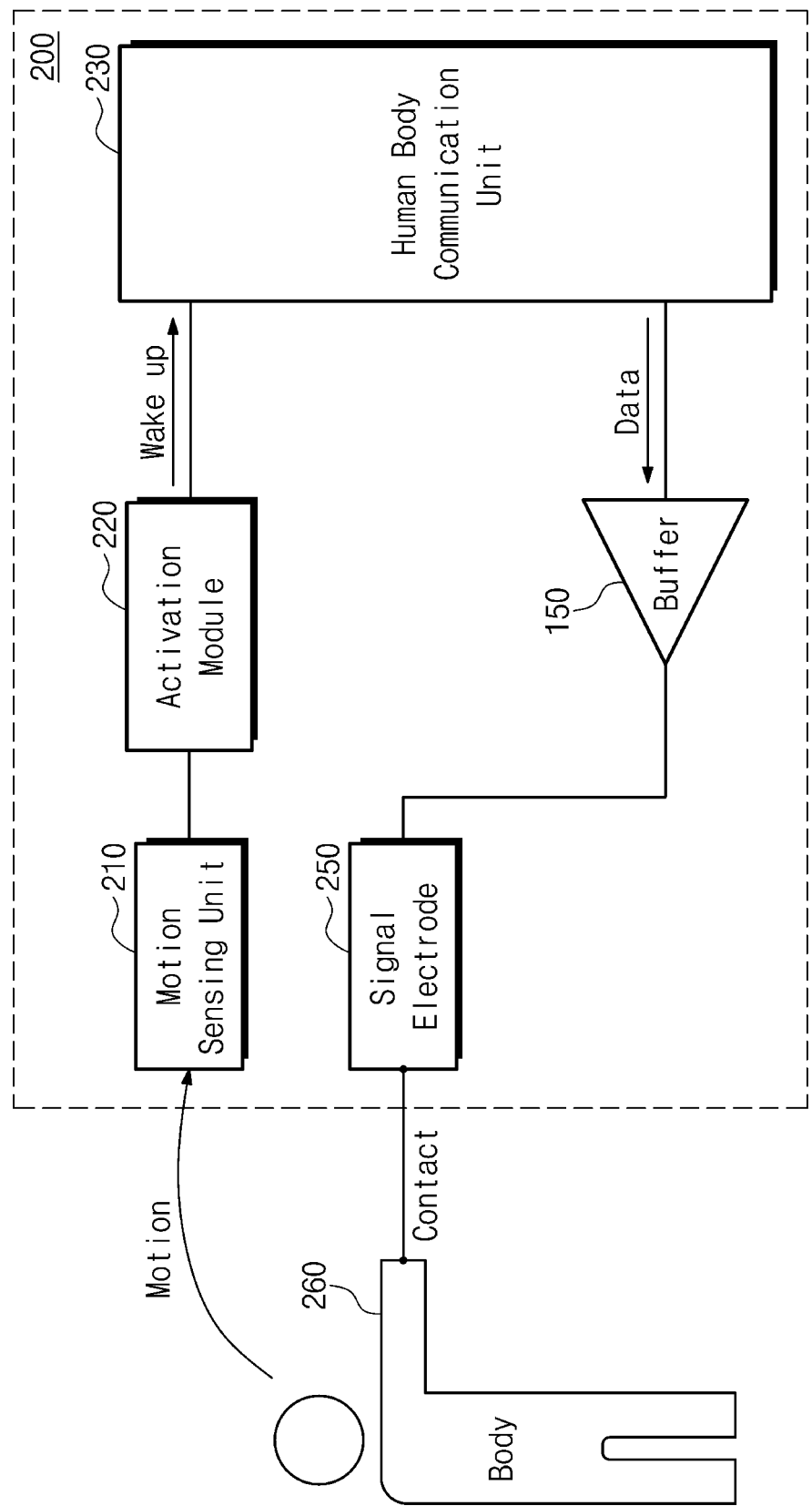
FIG. 11 is a diagram illustrating a human body sensing device according to an embodiment of the inventive concept.

FIG. 11 is a diagram illustrating a human body sensing device according to an embodiment of the inventive concept. Referring to FIG. 11, a human body sensing device 200 may include a motion sensing unit 210, an activation module 220, a human body communication unit 230, a buffer 240, and a signal electrode 250. Operations of the human body communication unit 230, the buffer 240, and the signal electrode 250 are similar to those described above, and thus additional description will be omitted to avoid redundancy.

The motion sensing unit 210 may sense a physical motion generated from an outside. For example, when a person presses a button of the human body sensing device 200, the button may correspond to the motion sensing unit 210. In this case, the button pressing motion by the person may correspond to the physical motion generated from the outside.

The activation module 220 may output the wake-up signal to the human body communication unit 230, based on a motion sensed by the motion sensing unit 210. For example, the activation module 220 may include a switch and a power supply device. In more detail, when a person presses the button of the human body sensing device 200, the power may be turned on when the switch inside the human body sensing device 200 is turned on, and the human body communication unit 230 may be activated based on the supplied power. In this case, the power supplied to the human body communication unit 230 may correspond to the wake-up signal.

In an exemplary embodiment, the motion sensing unit 210 of the human body sensing device 200 may be a motion detection sensor, the activation module 220 may output the wake-up signal to the human body communication unit 230, based on the motion sensed by the motion sensing unit 210. The wake-up signal output may be a digital signal of an electrical form.

Figure 12:
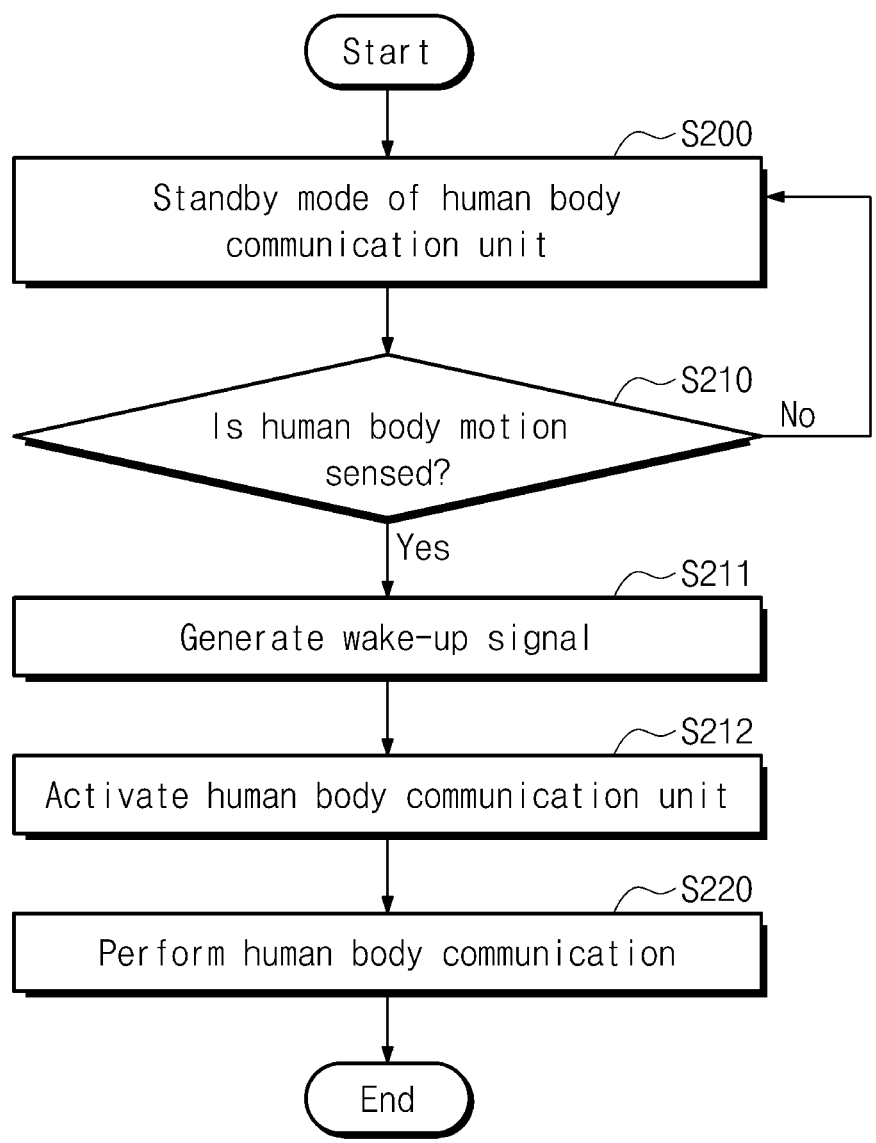
FIG. 12 is a flowchart describing an operation of a human body sensing device of FIG. 11.

FIG. 12 is a flowchart describing an operation of a human body sensing device of FIG. 11. For convenience of description, an operation according to the flowchart of FIG. 12 will be described with reference to the human body sensing device 200 of FIG. 11. Referring to FIGS. 11 and 12, the human body sensing device 200 may perform operation S200. Operation S200 is similar to operation S100 of FIG. 4, and thus, additional description will be omitted to avoid redundancy.

In operation S210, the motion sensing unit 210 may detect the physical motion from the outside. For example, when a human body motion is not sensed, the operation may return to operation S200. In an exemplary embodiment, when the human body motion is sensed, information indicating that the human body motion is sensed may be transferred to the activation module 220.

In operation S211, the activation module 220 may output the wake-up signal to the human body communication unit 230. In operation S212, the human body communication unit 230 may be activated, based on the received wake-up signal. In operation S220, the human body communication unit 230 may output the data signal, and the output data signal is transmitted to the body 260 through the buffer 240 and the signal electrode 250. Accordingly, the human body communication may be performed.

As described above, the human body sensing device 200 according to the embodiment of the inventive concept may switch from the standby state to the active state based on a specific motion of the human body. While the human body sensing device 100 of FIG. 3 simply obtains information indicating that a contact with the body occurs, the human body sensing device 200 may obtain information indicating that a specific motion occurs. That is, the human body sensing device 200 according to the embodiment of the inventive concept may allow a user to obtain detailed information related to the motion of the body.

Figure 13:
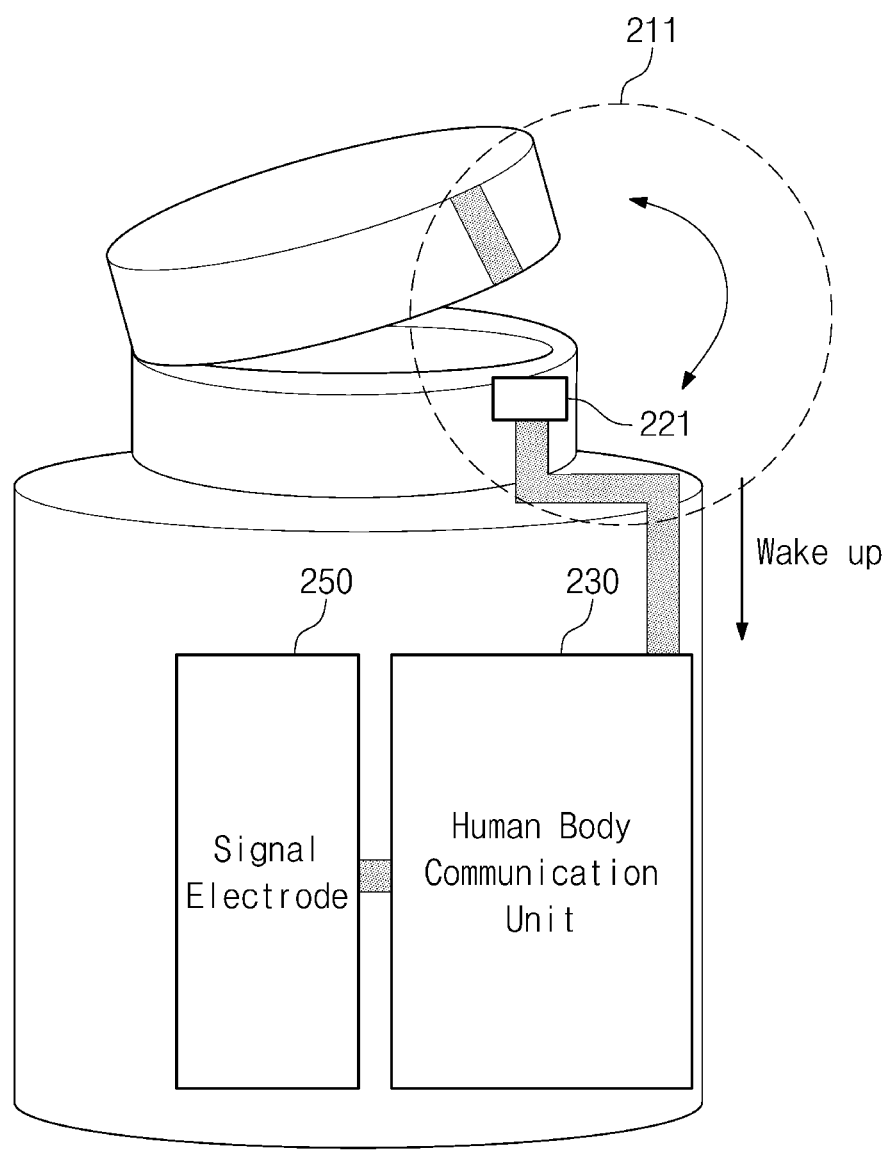
FIG. 13 is a diagram illustrating an operation of the human body sensing device of FIG. 11.

FIG. 13 is a diagram illustrating an operation of the human body sensing device of FIG. 11. Referring to FIG. 13, a human body sensing device according to an embodiment of the inventive concept may be implemented in a bottle. A motion sensing unit 211 may be a cap of the bottle, may sense the opening motion of the cap. An activation module 221 may be a switch attached to a cap surface of the bottle, may output the wake-up signal to the human body communication unit 230 when the opening motion of the cap is sensed.

As described above, the human body sensing device implemented in the bottle may sense the specific motion such as a motion of opening the cap. For example, when the human body sensing device is applied to a medicine bottle, it is difficult to determine that a patient has taken medicine only based on sensing the contact of the patient's body with the medicine bottle. In an exemplary embodiment, when the human body sensing device is applied to the medicine bottle, the motion of opening the cap of the medicine bottle may be sensed. Thus, reliable information on whether the patient has taken the medicine may be obtained.

Figure 14:
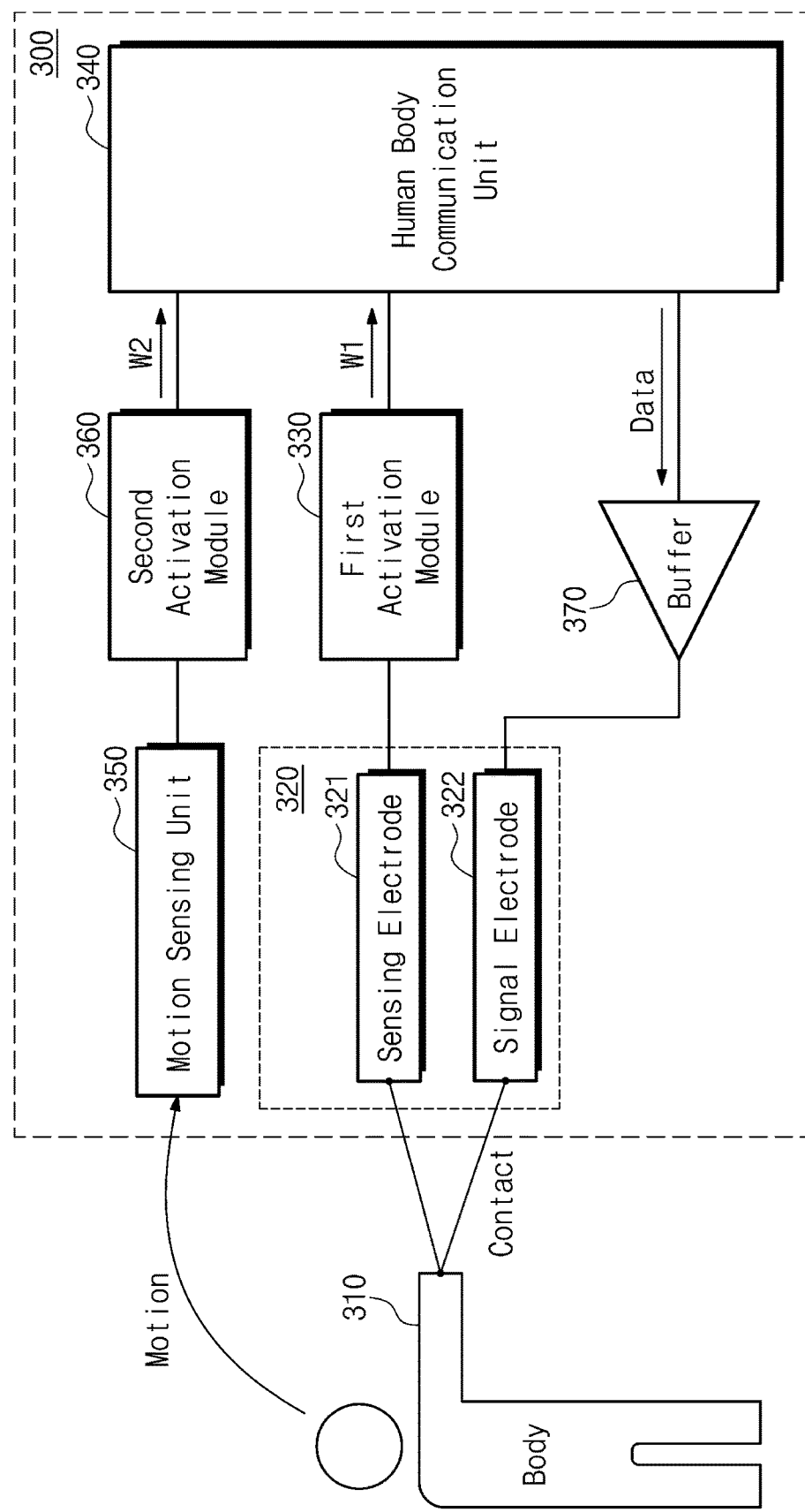
FIG. 14 is a diagram illustrating a human body sensing device according to an embodiment of the inventive concept.

FIG. 14 is a diagram illustrating a human body sensing device according to an embodiment of the inventive concept. Referring to FIG. 14, a human body sensing device 300 may include a contact sensing unit 320, a first activation module 330, a human body communication unit 340, a motion sensing unit 350, a second activation module 360, and a buffer 370. For convenience of description, with regard to the components described above, additional description will be omitted to avoid redundancy.

The first activation module 330 may sense a contact with a body 310 through the contact sensing unit 320, and may output a first wake-up signal W1 to the human body communication unit 340, based on a sensing result. The second activation module 360 may sense the human body motion through the motion sensing unit 350, and may output a second wake-up signal W2 to the human body communication unit 340, based on a sensing result. The human body communication unit 340 may receive the first wake-up signal W1 and the second wake-up signal W2, and may provide the data signal for performing the human body communication, based on the received signals W1 and W2.

As described above, as the human body sensing device 300 may determine whether to perform the human body communication in consideration of both the contact of the human body and the motion of the human body, when a possibility of the human body communication is low, an output of unnecessary data signals may be suppressed. For example, when only the contact of the human body occurs simply without an additional motion, the output of the data signal may be suppressed in the human body communication unit 340.

Figure 15:
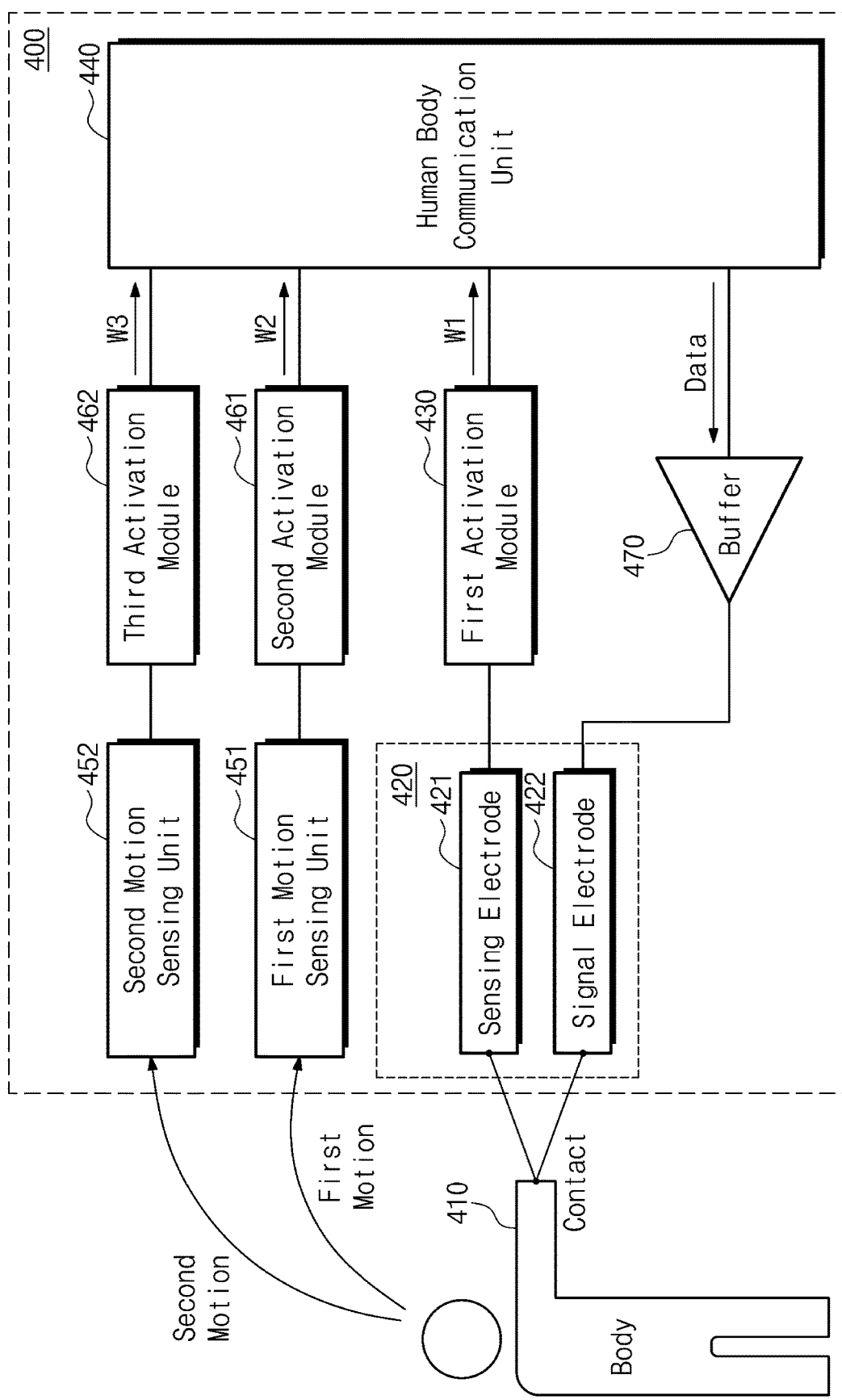
FIG. 15 is a diagram illustrating a human body sensing device according to an embodiment of the inventive concept.

FIG. 15 is a diagram illustrating a human body sensing device according to an embodiment of the inventive concept. Referring to FIG. 15, a human body sensing device 400 may include a contact sensing unit 420, a first activation module 430, a human body communication unit 440, a first motion sensing unit 451, a second activation module 461, a second motion sensing unit 452, a third activation module 462, and a buffer 470. For convenience of description, with regard to the components described above, additional description will be omitted to avoid redundancy.

The second activation module 461 may sense the first motion through the first motion sensing unit 451, and may output the second wake-up signal W2 to the human body communication unit 440, based on a result of sensing the first motion. The third activation module 462 may sense the second motion through the second motion sensing unit 452, and may output a third wake-up signal W3 to the human body communication unit 440, based on a result of sensing the second motion.

In an exemplary embodiment, the human body communication unit 440 may output the data signal when all of the first wake-up signal W1, the second wake-up signal W2, and the third wake-up signal W3 are received.

In an exemplary embodiment, the human body communication unit 440 may output the data signal related to the contact of the human body when receiving the first wake-up signal W1, output the data signal related to the first motion when receiving the second wake-up signal W2, and output the data signal related to the second motion when receiving the third wake-up signal W3.

In an exemplary embodiment, the human body communication unit 440 may further sense at least one motion in addition to the first motion and the second motion, and may further include at least one motion sensing unit and at least one activation module.

As described above, the human body sensing device 400 may sense a human body contact and a plurality of motions, thereby obtaining detailed and various information about the human body. In an exemplary embodiment, since the human body sensing device 400 may output a specific data signal corresponding to the sensed specific motion, the human body communication unit 440 may efficiently perform the human body communication.

Figure 16:
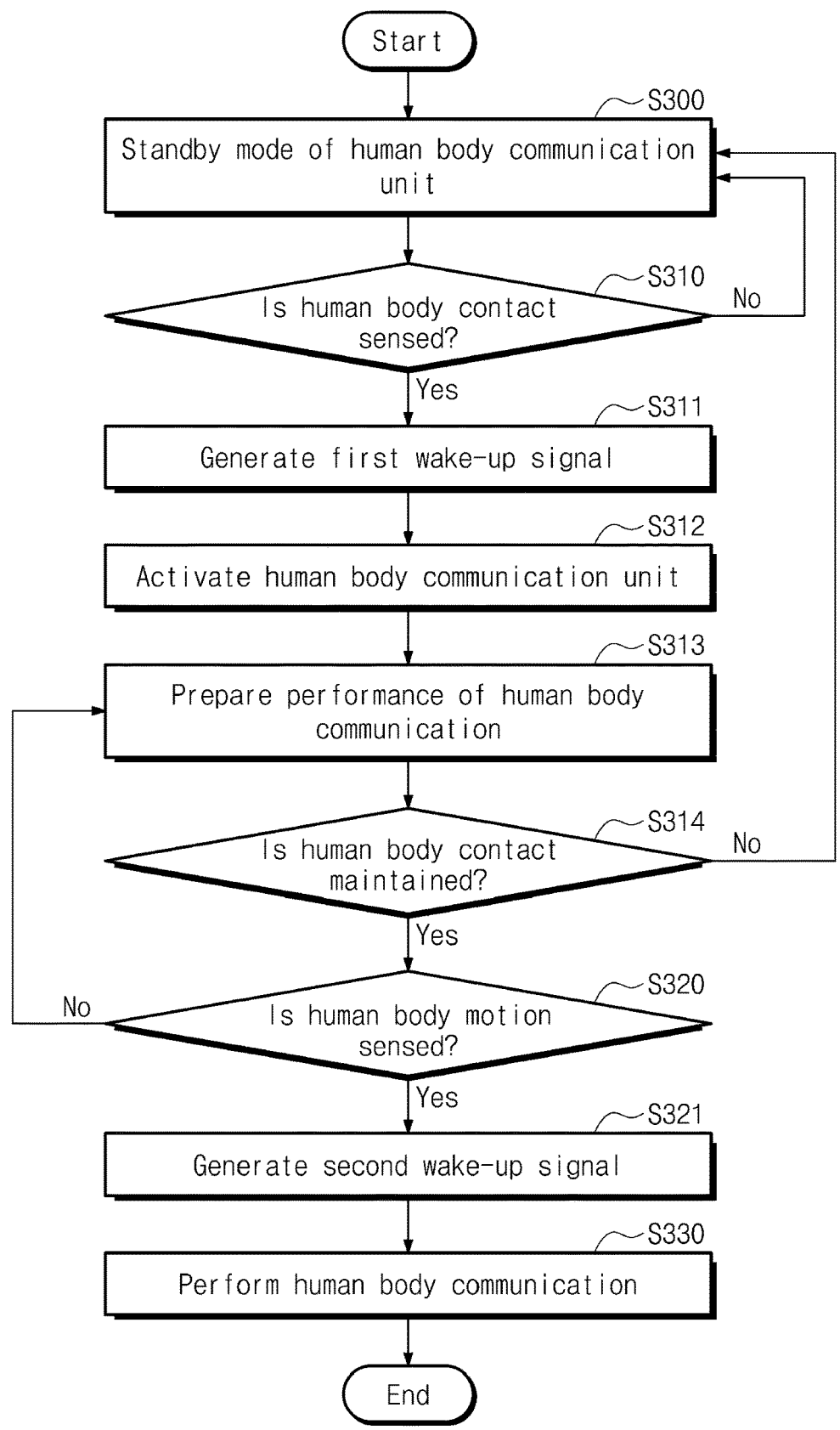
FIG. 16 is a flowchart describing an operation of a human body sensing device of FIG. 14.

FIG. 16 is a flowchart describing an operation of a human body sensing device of FIG. 14. For convenience of description, operations according to the flowchart of FIG. 16 will be described with reference to the human body sensing device 300 of FIG. 14. Referring to FIGS. 14 and 16, the human body sensing device 300 may perform operation S300. Operation S300 is similar to operation S100 of FIG. 4, and thus, additional description will be omitted to avoid redundancy.

In operation S311, the first activation module 330 may output the first wake-up signal W1 to the human body communication unit 340, based on a result of sensing the human body contact. In operation S312, the human body communication unit 340 may switch from the standby state to the active state. In operation S313, the human body communication unit 340 may prepare to perform the human body communication.

In operation S314, the human body communication unit 340 may output a signal for identifying whether the human body contact is maintained, and may determine whether the human body contact is maintained, by monitoring the voltage variation of a sensing electrode 321. For example, when the human body contact is released, the procedure may proceed to operation S300. In an exemplary embodiment, when the human body contact is maintained, the human body motion may be sensed.

In operation S320, the motion sensing unit 350 may sense the human body motion. For example, when the human body motion is not sensed, the procedure may proceed to operation S313. In an exemplary embodiment, when the human body motion is sensed, the motion sensing unit 350 may transfer information indicating that the human body motion is sensed to the second activation module 360.

In operation S321, the second activation module 360 may output the second wake-up signal W2 to the human body communication unit 340, based on a result indicating that the human body motion is sensed by the motion sensing unit 350.

In operation S330, the human body communication unit 340 may output the data signal for performing the human communication, based on the received first wake-up signal W1 and the received second wake-up signal W2. The output data signal may be transferred to the body 310 through a signal electrode 322, and the human body communication may be performed based on the transferred data signal.

In an exemplary embodiment, an operating method of the human body sensing device 300 may further include sensing another motion after operation S321. More specifically, the operating method may include operation S314 after operation S321, and may include sensing another motion. The operating method may return to operation S313 when another motion is not sensed, and may generate the third wake-up signal W3 and then move to operation S330 when the another motion is sensed.

In an example embodiment, after operation S321, a plurality of operations for sensing a plurality of other motions respectively may be further added.

As described above, the operating method of the human body sensing device 300 described in FIG. 16 includes operation S330 in which the human body communication is performed by the human body communication unit 340 that receives all the wake-up signals W1 and W2. Therefore, according to an embodiment of the inventive concept, the human body sensing device in which the performance of unnecessary communication is suppressed may be provided.

Figure 17:
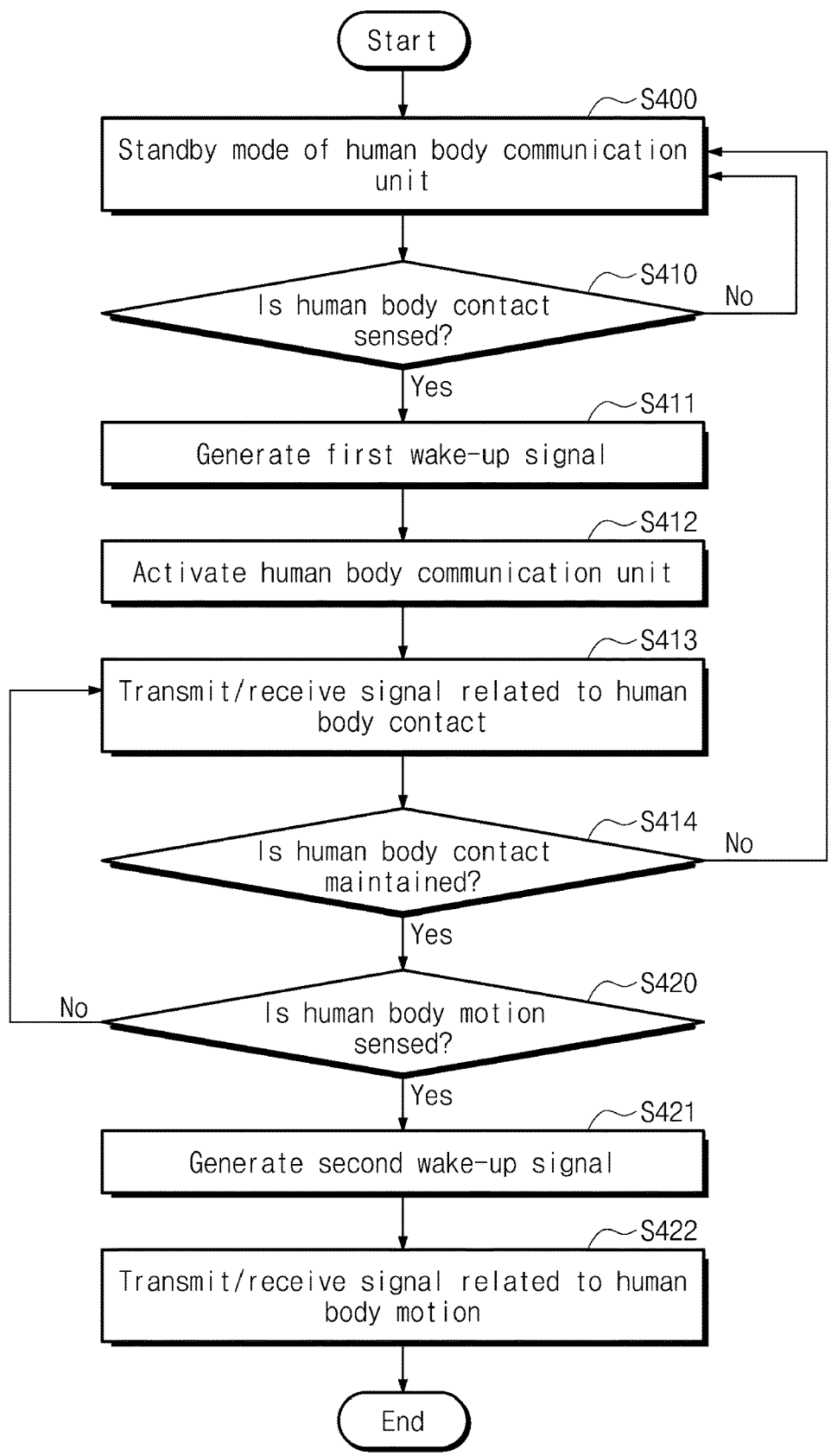
FIG. 17 is a flowchart describing an operation of a human body sensing device of FIG. 14.

FIG. 17 is a flowchart describing an operation of a human body sensing device of FIG. 14. For convenience of description, an operation according to the flowchart of FIG. 17 will be described with reference to the human body sensing device 300 of FIG. 14. Referring to FIGS. 14 and 17, the human body sensing device 300 may perform operation S400. Operations S400 to S412 are similar to operations S300 to S312 in FIG. 16, and thus additional descriptions will be omitted to avoid redundancy.

Referring to FIGS. 14 and 17, in operation S413, the human body communication unit 340 may output the data signal related to the contact, based on the received first wake-up signal W1. In operation S422, the human body communication unit 340 may output the data signal relating to the motion, based on the received second wake-up signal W2.

In an example embodiment, the operating method of the human body sensing device 300 may further include sensing another motion after operation S422. More specifically, the operating method may include operation S414 after operation S422 and may include sensing another motion. The operating method may return to operation S414 when another motion is not sensed, and may output the data signal related to the another motion when the another motion is sensed.

In an example embodiment, after operation S422, a plurality of operations for sensing a plurality of other motions respectively may be further added.

As described above, the operating method of the human body sensing device 300 described in FIG. 17 includes outputting the data (e.g., data related to contact) signal corresponding to the wake-up signal (e.g., W1) that the human body communication unit 340 receives. Therefore, according to an embodiment of the inventive concept, a human body sensing device for outputting the data signal corresponding to each of various human body information that is sensed may be provided.

According to an embodiment of the inventive concept, a human body sensing device having improved sensing reliability on a human body may be provided.

In addition, according to an embodiment of the inventive concept, a human body sensing device with a reduced manufacturing cost may be provided.

The contents described above are specific embodiments for implementing the inventive concept. The inventive concept may include not only the embodiments described above but also embodiments in which a design is simply or easily capable of being changed. In addition, the inventive concept may also include technologies easily changed to be implemented using embodiments. Therefore, the scope of the inventive concept is not limited to the described embodiments but should be defined by the claims and their equivalents.

What is claimed is:

1. A human body sensing device comprising:
a contact sensing unit including a sensing electrode and a signal electrode;
an activation module configured to sense a contact with a body through the sensing electrode when the sensing electrode and the signal electrode contact the body, and to output a wake-up signal in response to the sensing of the contact; and
a human body communication unit configured to provide a ground voltage to the signal electrode in a standby state, and to output a data signal to the signal electrode when the wake-up signal from the activation module is received;
wherein the activation module is further configured to cause the sensing electrode to be in a floating state in response to the wake-up signal.

2. The human body sensing device of claim 1, wherein the activation module includes:
a capacitor connected to the sensing electrode and charged to a reference voltage; and
a wake-up signal control module connected to the capacitor and configured to output the wake-up signal when a voltage of the capacitor is less than the reference voltage.

3. The human body sensing device of claim 2,
wherein the human body communication unit is further configured to output an activation signal when the wake-up signal is received,
wherein the wake-up signal control module includes a tri-state buffer, and
wherein the tri-state buffer is configured to output the wake-up signal, and to be in a floating state when the activation signal is received.

4. The human body sensing device of claim 1, further comprising:
a human body matching network configured to receive the data signal, to output the received data signal to the signal electrode, and to perform impedance matching with the body.

5. The human body sensing device of claim 1, wherein the human body communication unit is further configured to operate in a first state when the wake-up signal is received and in a second state when a release of the contact with the body is sensed.

6. The human body sensing device of claim 5, further comprising:
a ground control unit configured to release a connect of the signal electrode and a ground point in the first state and to connect the signal electrode to the ground point in the second state.

7. The human body sensing device of claim 5,
wherein the human body communication unit further includes a signal generator connected to a power supply voltage and a ground voltage, and
wherein the signal generator is configured to output the data signal in the first state and to output the ground voltage in the second state.

8. The human body sensing device of claim 7, wherein the human body communication unit further includes:
a monitor unit configured to monitor a voltage of the sensing electrode; and
a counter unit configured to count a falling edge of the voltage of the sensing electrode monitored from the monitor unit in the first state.

9. The human body sensing device of claim 8, wherein the human body communication unit further includes a processor configured to output information indicating that the contact with the body is maintained, when the falling edge is counted.

10. The human body sensing device of claim 9, wherein the processor calculates a time for which the contact is maintained, based on the information indicating that the contact is maintained and the wake-up signal.

11. A human body sensing device comprising:
a contact sensing unit including a sensing electrode and a signal electrode;
an activation module configured to sense a contact with a body through the sensing electrode when the sensing electrode and the signal electrode contact the body, and to output a wake-up signal in response to the sensing of the contact; and a human body communication unit configured to provide a ground voltage to the signal electrode in a standby state, and to output a data signal to the signal electrode when the wake-up signal from the activation module is received, wherein the human body communication unit is further configured to output a clock signal, wherein the activation module includes a wake-up signal control module, and wherein the wake-up signal control module is configured to receive the clock signal, to output the received clock signal to the sensing electrode, and to output the wake-up signal when the clock signal output to the sensing electrode is distorted.

12. The human body sensing device of claim 11, wherein the wake-up signal control module switches to a floating state after the wake-up signal is output.

13. A human body sensing device comprising:
a contact sensing unit including a sensing electrode and a signal electrode;
a first activation module configured to sense a contact with a body through the sensing electrode when the sensing electrode and the signal electrode contact the body, and to output a first wake-up signal in response to the sensing of the contact;
a first motion sensing unit configured to sense a first motion of the body;
a second activation module configured to output a second wake-up signal, based on the sensed first motion; and
a human body communication unit configured to receive the first wake-up signal in a first state, to switch to a second state based on the received first wake-up signal, to receive the second wake-up signal in the second state, and to output a data signal, and wherein the signal electrode outputs a ground voltage in the first state, and outputs the data signal to the body in the second state.

14. The human body sensing device of claim 13, further comprising:
a second motion sensing unit configured to sense a second motion different from the first motion of the body; and
a third activation module configured to output a third wake-up signal that is different from the first wake-up signal and the second wake-up signal to the human body communication unit, based on the sensed second motion, and wherein the data signal is output based on the first wake-up signal, the second wake-up signal, and the third wake-up signal that is output from the third activation module.

15. The human body sensing device of claim 14, wherein the human body communication unit outputs the data signal when both the first wake-up signal and the second wake-up signal are received.

16. The human body sensing device of claim 14,
wherein the data signal includes a first data signal and a second data signal, and
wherein the human body communication unit outputs the first data signal when the first wake-up signal is received, and outputs the second data signal when the second wake-up signal is received.

* * * * *